United States Patent
Ramer et al.

(10) Patent No.: US 9,696,200 B2
(45) Date of Patent: Jul. 4, 2017

(54) COMBINATORIAL LIGHT DEVICE FOR GENERAL LIGHTING AND LIGHTING FOR MACHINE VISION

(71) Applicant: ABL IP HOLDING LLC, Conyers, GA (US)

(72) Inventors: David P. Ramer, Reston, VA (US); Jack C. Rains, Jr., Herndon, VA (US); Januk Aggarwal, Tysons Corner, VA (US)

(73) Assignee: ABL IP HOLDING LLC, Conyers, GA (US)

( * ) Notice: Subject to any disclaimer, the term of this patent is extended or adjusted under 35 U.S.C. 154(b) by 382 days.

(21) Appl. No.: 14/285,931

(22) Filed: May 23, 2014

(65) Prior Publication Data
US 2015/0338268 A1 Nov. 26, 2015

(51) Int. Cl.
| | |
|---|---|
| *G01J 1/08* | (2006.01) |
| *G01N 21/55* | (2014.01) |
| *G01N 21/64* | (2006.01) |
| *G01J 1/18* | (2006.01) |
| *F21V 33/00* | (2006.01) |
| *F21V 7/00* | (2006.01) |
| *F21Y 115/10* | (2016.01) |
| *F21Y 113/13* | (2016.01) |

(52) U.S. Cl.
CPC .............. *G01J 1/08* (2013.01); *F21V 7/0008* (2013.01); *F21V 33/00* (2013.01); *G01J 1/18* (2013.01); *G01N 21/55* (2013.01); *G01N 21/64* (2013.01); *F21Y 2113/13* (2016.08); *F21Y 2115/10* (2016.08)

(58) Field of Classification Search
CPC .... G01J 1/08; G01J 1/18; F21V 33/00; G01N 21/55; G01N 21/64
See application file for complete search history.

(56) References Cited

U.S. PATENT DOCUMENTS

| | | | |
|---|---|---|---|
| 4,091,441 | A | 5/1978 | Ott |
| 5,877,490 | A | 3/1999 | Ramer et al. |
| 5,914,487 | A | 6/1999 | Ramer et al. |
| 6,995,355 | B2 | 2/2006 | Rains et al. |
| 8,021,008 | B2 | 9/2011 | Ramer |

(Continued)

OTHER PUBLICATIONS

FAWK3S, Finding Blood with UV Light, Mar. 20, 2010, http://www.physicsforums.com/showthread.php?t=388224.

(Continued)

*Primary Examiner* — Tony Ko
(74) *Attorney, Agent, or Firm* — RatnerPrestia

(57) ABSTRACT

A system with a machine and a lighting device. The machine includes an image capture device and a machine vision processing system configured to detect a characteristic of a subject in a space for an operation of the machine. The lighting device includes a first light source for generating light to illuminate the space, and a second light source for generating light of a particular wavelength to support detection of the characteristic of the subject via the machine vision processing system. The light of the particular wavelength is output at a sufficient intensity reasonably expected to produce a particular emission from the subject detectable via the image capture device different from an emission produced by exposure of the subject to the light for illumination of the space. The first and second light sources are integrated into the lighting device.

20 Claims, 9 Drawing Sheets

(56) References Cited

U.S. PATENT DOCUMENTS

| | | | |
|---|---|---|---|
| 8,172,424 | B2 | 5/2012 | Phipps et al. |
| 8,205,998 | B2 | 6/2012 | Ramer et al. |
| 8,282,241 | B2 | 10/2012 | Ramer et al. |
| 8,330,373 | B2 | 12/2012 | Ramer et al. |
| 8,334,644 | B2 | 12/2012 | Ramer et al. |
| 2008/0013335 | A1 | 1/2008 | Tsutsumi |
| 2011/0307035 | A1 | 12/2011 | Tsao |
| 2012/0327656 | A1 | 12/2012 | Ramer et al. |
| 2013/0049602 | A1 | 2/2013 | Raj et al. |
| 2014/0035472 | A1 | 2/2014 | Raj et al. |

OTHER PUBLICATIONS

Noureddine, Maher, Forensic Tests for Semen: What You Should Know, Oct. 19, 2011, http://ncforensics.wordpress.com/2011/10/19/forensic-tests-for-semen-what-you-should-know/.

Photonics.com, "207-nm UV Light May Reduce Surgical Infections", Oct. 17, 2013, http://www.photonics.com/Article.aspx?AID=55109.

Koninklijke Philips Electronics N.V., "HealWell—A New Lighting Solution for Patient Rooms", Dec. 2011, http://www.lighting.philips.com/pwc_li/main/application_areas/assets/pdf/healwell-brochure-int.pdf.

Lighting Research Center, "Red Light Increases Alertness During 'Post-Lunch Dip'", Apr. 22, 2013, http://www.Lrc.rpi.edu/resources/newsroom/pr_story.asp?id=253.

Photonics.com, "CLEO Presents Cutting-Edge Research on Optics, Lasers", Jun. 7, 2013, http://www.photonics.com/Article.aspx?AID=54092.

Airocide.com, 2013, https://ww.airocide.com/.

Tuner, Jan, "Laser Dentistry/Low Level Therapeutic Lasers Expand the Scope of Dentistry", Sep. 1, 2010, http://www.bloopticsworld.com/articles/print/volume-3/issue-5/features/laser-dentistry-low-level-laser-therapy-therapeutic-lasers-expand-the-scope-of-dentistry.html.

Goode, Barbara, "LaserLight Therapy/Hair Restoration: Crowdfunding Succeeds for At-Home Laser Hair-Growth Device", Sep. 25, 2013, http://www.bloopticsworld.com/articles/print/volume-6/issue-5/departments/news-notes/laser-light-therapy-hair-restoration-crowdfunding-succeeds-fir-at-home-laser-hair-growth-device.html.

Non Final Office Action for U.S. Appl. No. 14/286,065, mailed Jul. 29, 2016, 11pages.

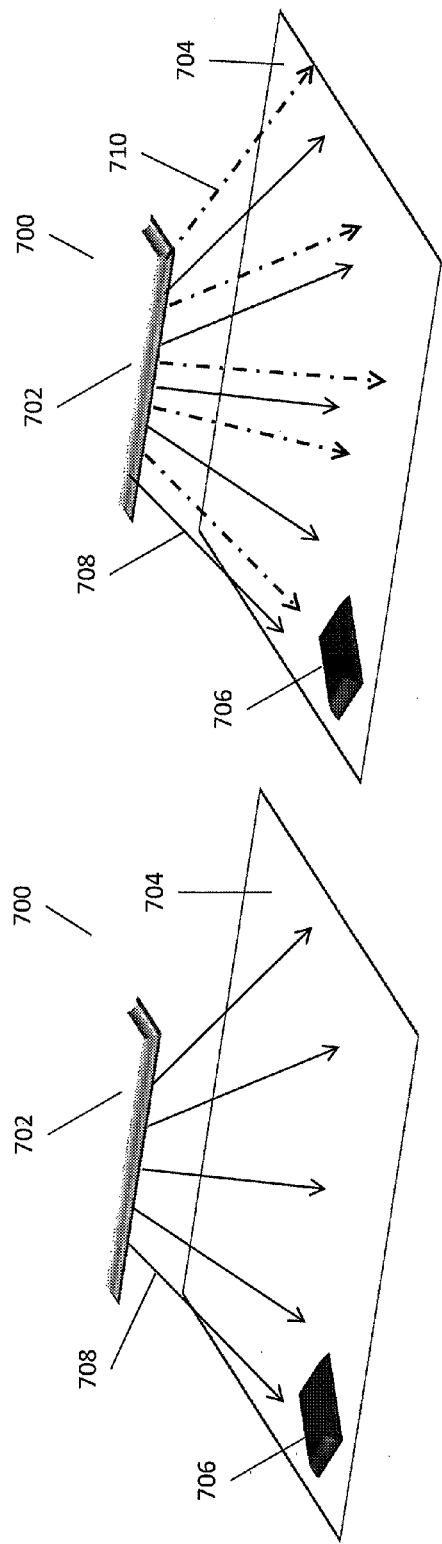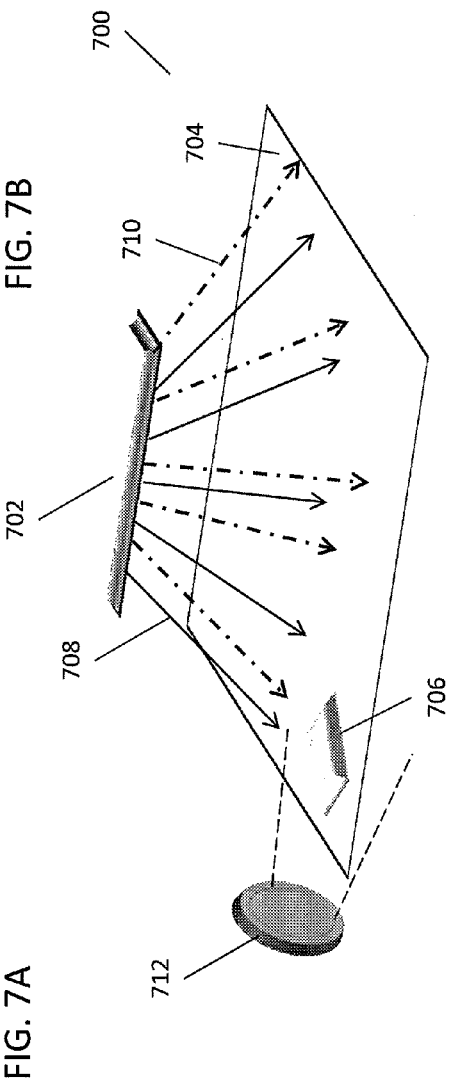
FIG. 7A
FIG. 7B
FIG. 7C

COMBINATORIAL LIGHT DEVICE FOR GENERAL LIGHTING AND LIGHTING FOR MACHINE VISION

TECHNICAL FIELD

The examples discussed below relate to techniques and equipment to provide a light source for general illumination of a space and an additional light source to provide light of a particular wavelength to produce a particular emission from a subject different from an emission produced by exposure of the subject to the light for general illumination of the space and image capture for machine vision processing, e.g. to detect a characteristic of the subject in the space.

BACKGROUND

In recent years, demand has arisen for lighting systems that produce light for purposes other than general illumination. Multiple lighting devices are used for such alternative purposes. For example, many lights are designed to produce only a particular wavelength of light, such as ultraviolet, infrared, or particular wavelengths of visible light with an increased intensity versus that of general illumination lights. Many benefits are associated with the particular wavelengths, such as producing a particular emission from subjects different from emissions produced by exposure of the subjects to general illumination light, and such emissions can be used for a wide range of machine vision applications, such as object detection, machine guidance, and the like.

The need to produce these additional wavelengths at sufficient intensities leads to many applications where multiple lighting fixtures are used. Users will often have a device for general illumination, and an additional device for generating the preferred wavelength of light can be used for machine vision applications. For example, in a plant that uses machines with infrared (IR) responsive controls, there will be devices to illuminate the plant floor-space for factory workers as well as separate IR lighting for detection by the image capture and associated machine vision systems of the various machines on the factory floor. The requirement to have multiple lighting devices is not convenient in most many applications. For example, installation of multiple lighting fixtures in a single room may not be feasible as the room may not be designed to incorporate more than one lighting device.

SUMMARY

Hence a need exists for a lighting device or system with such a device, where the single lighting device can generate light for general illumination and can generate light of one or more particular wavelengths that can support a machine vision application.

The equipment and techniques disclosed herein address one or more of the above noted problems or needs with respect to integrated lighting devices for multiple purposes.

As disclosed herein, an example of a system includes a machine and a lighting device. The machine can include an image capture device and a machine vision processing system, configured to detect a characteristic of a subject in a space responsive to input from the image capture device for operation of the machine at least in part based on detection of the characteristic of the subject. The lighting device in the example includes a first light source configured to generate light for illumination of the space and a second light source to generate light of a particular wavelength independent from the light for illumination. The light of the particular wavelength may support the detection of the characteristic of the subject via the machine vision processing system. The light of the particular wavelength can be output from the lighting device at a sufficient intensity reasonably expected to produce a particular emission from the subject detectable via the image capture device and that is different from an emission produced by exposure of the subject to the light for illumination output from the lighting device. The first and second light sources can be integrated into the same lighting device.

Another example discussed in the detailed description relates to a method that involves generating light for illumination of a space with a first light source integrated into a lighting device, and generating light of a particular wavelength from a second light source integrated into the lighting device independently from the light for illumination to support detection of a characteristic of a subject via a machine vision processing system of a machine. Further, the light of the particular wavelength is output from the lighting device at a sufficient intensity reasonably expected to produce a particular emission from a subject in the space detectable via an image capture device in the machine that is different from an emission produced by exposure of the subject to the light for illumination. Input from an image capture device is received via the machine vision processing system that includes the particular emission from the subject detected by the image capture device. A characteristic of the subject in the space may be detected via the machine vision processing system from the received input. The operation of the machine can be controlled at least in part based on the detected characteristic of the subject.

A further disclosed example relates to a system that includes a machine, a pixelated screen and a light source configured to project light toward the pixelated screen. The machine may include an image capture device and a machine vision processing system configured to detect a characteristic of a subject in a space responsive to input from the image capture device for an operation of the machine at least in part based on the detection of the characteristic of the subject. A first set of pixels in the screen may be adapted to generate light for illumination of the space, and a second set of pixels may be adapted to generate and emit light of a particular wavelength to support the detection of the characteristic of the subject via the machine vision processing system. The light of the particular wavelength can be output at a sufficient intensity reasonably expected to produce a particular emission from the subject detectable via the image capture device different from an emission produced by exposure of the subject to the light for illumination of the space.

Additionally, a lighting device may include a first light source configured to generate light for illumination of a space and a second light source configured to generate, independent from the light for illumination, light of a particular wavelength to support detection of a characteristic of a subject for responsive control of a machine. The light of the particular wavelength can be output at a sufficient intensity reasonably expected to produce a particular emission from the subject different from an emission produced by exposure of the subject to the light for illumination. The first and second light source are integrated into the lighting device.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 7A-7C are illustrations of systems showing particular emissions being produced and detected by an image capture device.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
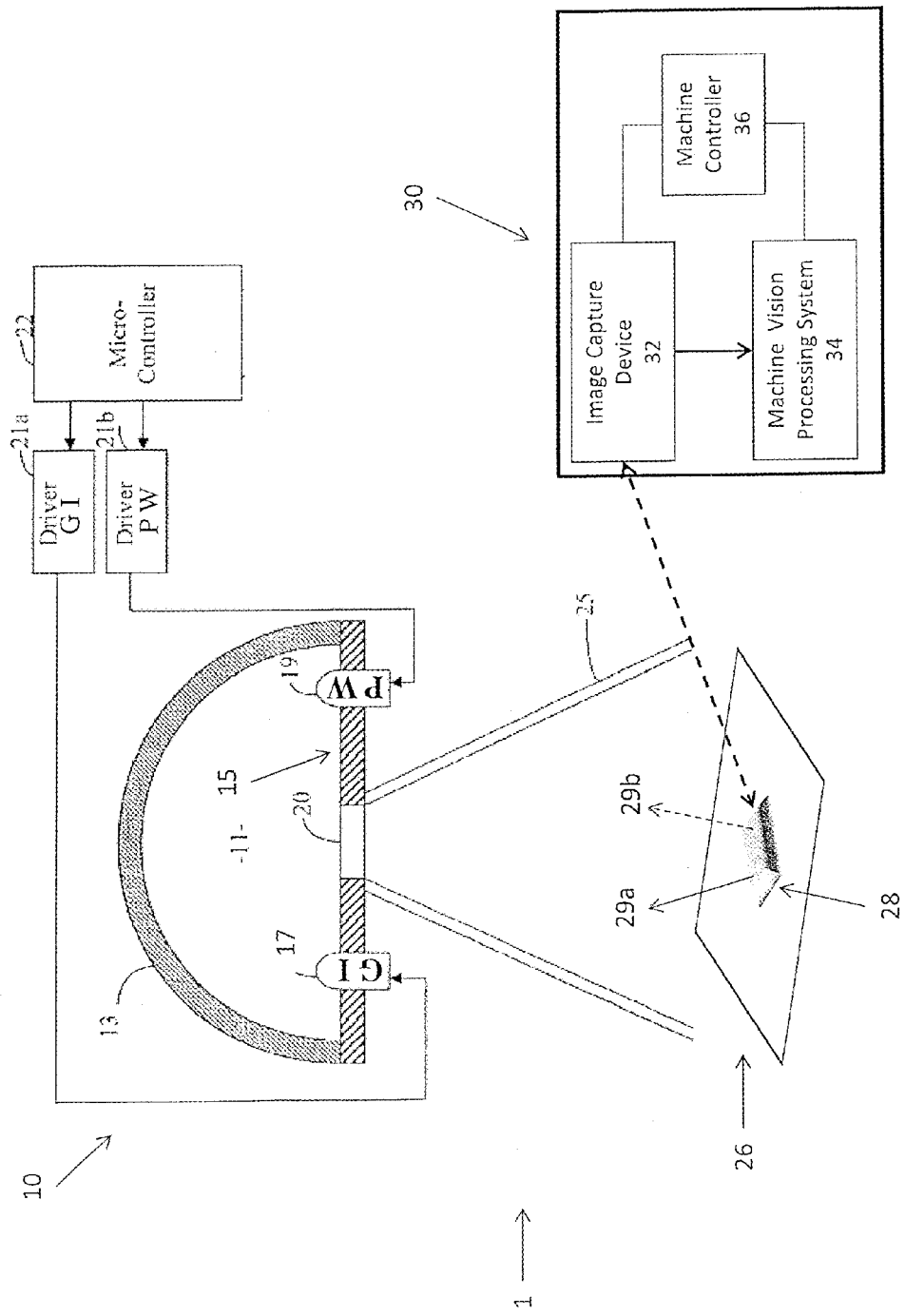
FIG. 1 illustrates an example of a system with a lighting device for general illumination as well as illumination with one or more particular wavelengths, a space and a machine with certain elements thereof shown in cross-section.

Reference now is made in detail to the examples illustrated in the accompanying drawings and discussed below. FIG. 1 illustrates a system 1 including a cross-sectional illustration of a lighting device 10 that emits light in a space 26, and a functional block diagram representing a machine 30 that controls one or more operations thereof via machine vision. Elements shown in the drawing are sized and positioned for ease of illustration and are not drawn to scale or shown separated in a precise manner as might be used in an actual device. Although the drawing shows one lighting device 10 and one machine 30, a system 1 like that shown may have any number of lighting devices 10 for the space 26 and/or may have any number of machines 30 using machine vision control within the space 26 illuminated by or receiving emissions from the lighting device(s) 10 of the system 1. There may also be other lighting devices and/or machines in the vicinity, some of which may or may not be involved in machine vision in the manner described below relative to device 10 and machine 30.

The device 10 is intended for general lighting applications in areas or regions intended to be occupied by one or more persons, subjects, and/or machines that will see by or be exposed to the general illumination light provided by the system 1, and for outputting light of a particular wavelength at a sufficient intensity and for a sufficient duration reasonably expected to produce a particular emission from a subject 28 different from an emission produced by exposure of the subject 28 to the light for illumination. As used herein, "emission from the subject" encompasses reflection of light from the subject in the visible spectrum region and other regions of the light spectrum, opto-luminescence such as fluorescence or phosphorescence in various spectral regions, filtered transmission of visible or other light, and other types of light generation in response to illumination of the subject. The emission from the subject, however, will be different when exposed to PW light outputted from the lighting device from that when exposed to GI light. When exposed to PW light, the particular emission from the subject should be sufficient so as to support use of the emission in response to the PW light for a machine vision application.

The lighting devices may include lighting fixtures, such as ceiling fixtures, table lamps, desk lamps, etc. It will be understood that the disclosed lighting devices can be implemented in various types of lighting fixtures, lighting systems, and other lighting apparatus. The particular emission from the subject 28 may be of a wavelength in the visible spectrum and/or outside the visible spectrum. For example, for task lighting applications, the lighting device 10 outputs light in the visible spectrum for general illumination, which often will appear relatively white to occupants of the space 26; but lighting device 10 may also output light of the particular wavelength(s) for producing the particular emission from a subject 28 and for supporting detection of a characteristic of the subject 28 by the machine 30 for its machine vision based control functions. The lighting device output of the wavelength(s) in support of machine vision may be generated simultaneously to and/or independently from the general illumination emission.

There may be some difference of opinion among technical practitioners as to the light characteristics needed to produce a particular emission from a subject, e.g. the wavelength, duration and intensity of exposure of the subject to particular wavelength band light needed to produce a particular emission for sensing by machines for machine vision applications. The technologies under discussion here are intended to deliver light for a general illumination purpose and light of wavelength(s) for producing a particular emission from a subject with a device integrating sources for both purposes and typically through the same output path of the lighting device. Although the light characteristics are intended to produce the particular emission, the present disclosure is not limited either to any particular standard or magnitude of lighting parameters that different authorities may feel are required to fully produce a particular emission from a subject different from an emission produced by exposure of a subject to general illumination light. Additionally, a given machine will likely have specifications for minimal lighting requirements that the machine manufacturer warrants will suffice for use of the machine vision control system. Different machines, manufacturers and/or applications will have different requirements to be met by the lighting devices and/or other components of the disclosed systems such that various parameter values may be necessary for the components, and differing or less than optimal results may occur. Machine vision may work at somewhat lower parameter values, but may not be optimal if so operated.

Furthermore, it will be understood the particular emission from a subject may not be fully produced and the characteristics of the subject may not be adequately detected due to circumstances unrelated to the operation of the systems, lighting devices, or machines. For instance, producing the particular emission and detecting the characteristic may require a subject to be exposed to the particular wavelength for a given time such that the emission may not be produced if, for example, the subject is prematurely removed from exposure, the machine is not within viewing range of the subject, additional light sources alter the particular emission, the machine is improperly calibrated to the particular emission, etc. As another example, studies and manufacturers may suggest various parameter settings for the lighting devices and/or machines (e.g. wavelength, intensity, and/or duration of the particular wavelength, tuning of the image capture device, etc.) which may be incompatible with machine or lighting device specifications, and following such suggestions may lead to improper emission production and/or characteristic detection.

The lighting devices of the systems disclosed herein are capable of outputting particular wavelengths at a sufficient intensity, sufficient duration, and/or otherwise proper characteristic to at least partially produce a particular emission from the subject absent unrelated interfering circumstances, and are thus reasonably expected to produce the particular emission from the subject intended to facilitate machine vision related detection. Furthermore, the machines of the systems disclosed herein are capable of machine vision operation by detecting a characteristic of a subject from the produced particular emissions, and thus, the light of the particular wavelength(s) supports the detection of the characteristics of the subject via machine vision processing systems of the machines disclosed herein. For many particular wavelength output(s), the outputs of the appropriate wavelength(s) will exhibit a sufficient intensity to produce the particular emission and will exhibit one or more other characteristics of sufficient values to produce the particular emission, such as a sufficient one or more of: duration, intensity variation rate (e.g. flash rate).

In examples of system 1 of FIG. 10, a lighting device 10 includes an optical element coupled to receive light from the sources and configured to provide an output of light for the device, where light from both sources emerge via the same device output. The two types of light from the light sources may be output from the output at different times, or in other examples, the two types of light emerge via the same output more or less simultaneously. The optical element serves to direct light from multiple light sources integrated within the respective lighting device to the light output of the device. If output simultaneously, the optical element combines the multiple types of light for output via the optical output of the lighting device.

Hence, the system 1 using lighting device 10 combines light from multiple sources, and for that purpose, most examples of lighting devices include an optical light mixer, such as a diffuser. In the example of FIG. 1, the illustrated system 10 includes an optical cavity 11 having a diffusely reflective interior surface to receive and combine radiant energy of different colors/wavelengths. The cavity 11 may have various shapes. The illustrated cross-section would be substantially the same if the cavity is hemispherical or if the cavity is semi-cylindrical with the cross-section taken perpendicular to the longitudinal axis. The optical cavity in the examples discussed below is typically an optical integrating cavity.

The disclosed lighting devices that have a cavity as the optical mixer may use a variety of different structures or arrangements for the optical integrating cavity. At least a substantial portion of the interior surface(s) of the cavity exhibit(s) diffuse reflectivity. It is desirable that the cavity surface have a highly efficient reflective characteristic, e.g. a reflectivity equal to or greater than 90%, with respect to the relevant wavelengths. In the example of FIG. 1, the surface is highly diffusely reflective to energy in the visible, near-infrared, and ultraviolet wavelengths.

The cavity 11 may be formed of a diffusely reflective plastic material, such as a polypropylene having a 97% reflectivity and a diffuse reflective characteristic. For purposes of the discussion, the cavity 11 in the device 10 is assumed to be hemispherical. In the example, a hemispherical dome 13 and a substantially flat cover plate 15 form the optical cavity 11. At least the interior facing surfaces of the dome 13 and the cover plate 15 are highly diffusely reflective, so that the resulting cavity 11 is highly diffusely reflective with respect to the radiant energy spectrum produced by the device 10. As a result, the cavity 11 in the example of FIG. 1 is an integrating type optical cavity. Although shown as separate elements, the dome and plate may be formed as an integral unit.

The optical integrating cavity 11 has an optical aperture 20 for allowing output of combined light energy (e.g., the combined general illumination light and the particular wavelength light). In the example, the aperture 20 is a passage through the approximate center of the cover plate 15, although the aperture may be at any other convenient location on the plate 15 or the dome 13. The aperture is transmissive to light. Although shown as a physical passage or opening through the wall or plate of the cavity, those skilled in the art will appreciate that the optical aperture may take the form of a light transmissive material, e.g. transparent or translucent, at the appropriate location on the structure forming the cavity 11.

Because of the diffuse reflectivity within the cavity 11, light within the cavity is integrated before passage out of the optical aperture 20. In the examples, the device 10 is shown outputting the combined light downward through the aperture 20, for convenience. However, the device 10 may be oriented in any desired direction to perform a desired application function, for example, to provide general illumination and other particular lighting to persons in a particular direction or location with respect to the lighting device 10 or to illuminate or provide particular wavelength(s) to a different surface such as a wall, floor, desk, bed or table top.

Also, the optical integrating cavity 11 may have more than one aperture 20, for example, oriented to allow output of integrated light in two or more different directions or regions. The device 10 and/or the aperture(s) 20 may additionally be oriented or positioned such that the light of the particular wavelength for the particular emission is output in a particular direction or location with respect to the lighting device or output to target a different surface such as a wall, floor, table, or other subject in the space, such as a hospital bed, a body part of a human, obstructions in the space, etc.

In the example, the cavity 11 appears empty, e.g. as if filled with air. It is also contemplated that a wide range of other cavity structures may be used, including structure in which the cavity is partially filled with an optically transmissive liquid or solid. In that regard, just a few of many examples of other lighting device arrangements with alternative cavity structures may be found in U.S. Pat. Nos. 8,282,241; 8,172,424; 8,205,998 and 8,021,008, the full patent disclosures of which are incorporated entirely herein by reference.

Light sources 17 to 19 supply light into the interior of the optical integrating cavity 11 and are both integrated into the device 10. Light source 17 generates light for general illumination (GI) of a space and light source 19 generates light of a particular wavelength (PW) for a particular emission from a subject different from an emission produced by exposure of the subject to GI light. The cavity 11 effectively integrates the energy of the GI light and the PW light so that the integrated or combined light energy output through the aperture 20 includes the radiant energy of the GI light and the PW light in relative amounts substantially corresponding to the relative intensities of input into the cavity 11.

For simplicity, the example shows a single source of each type. Depending on the technology and/or the variety of particular wavelengths offered by the device 10, there may be any number of each type of light source. The general illumination source 17 may be implemented using one or more emitters of white light, a combination of emitters of white light and emitters of light intended to adjust or improve the color characteristic(s) of the white light or by a number of sources of different colors (e.g. red, green and blue) that can be combined by the cavity 11 to produce light that is sufficiently white to support the general illumination function of the device 10. Each included particular wavelength (PW) source 19 outputs light of some wavelength range about a nominal rated wavelength, e.g. around 540 nanometers (nm), around 1300 nm, about a nominal wavelength in the 320-340 nm, around 207 nm, around 260 nm, and/or other wavelengths (e.g., near infrared of about 720 nm to about 1000 nm, short wave infrared (SWIR) of about 1000 nm to about 3000 nm, ultraviolet of about 100 nm to about 400 nm, near ultraviolet of about 380 nm to about 420 nm, etc.) reasonably expected to produce a particular emission of a subject different from an emission produced by exposure of the subject to GI light when the PW light is output at a sufficient intensity and/or with other sufficient characteristic(s).

Control of the intensity of output of the GI light source 17 and the PW light source 19 sets a spectral characteristic of the combined GI light and the PW light output through the aperture 20 of the optical integrating cavity. Although other types of light emitters may be used for either one or both of the sources 17, 19, for purposes of further discussion, we will assume that each source 17 or 19 utilizes one or more light emitting diodes (LEDs).

The microcontroller 22 may be responsive to a number of different control input signals. For example, microcontroller 22 may be responsive to one or more user inputs of various types. Further, the microcontroller 22 may be responsive condition sensors, e.g. providing information relating to feedback about operations the LED light sources 17 to 19 and/or sensing conditions of lighting or subjects in the space to be illuminated by the device. Feedback may be provided through the photo sensing device (not shown), for example, to detect overall intensity of light output or information about color characteristics of light in the cavity or output via the aperture. Depending on the application of the device 10, different types of optical feedback sensing may be provided, relative to light generated for illumination and/or particular wavelength light. It may also be desirable to sense temperature of or around one or both light sources. Other condition sensors may provide input information about one or more conditions in the illuminated space. Although not shown, a sensor, for example, might detect occupancy; whereas another sensor might detect ambient light level.

The device 10 includes a driver 21a for the GI light source 17 and a driver 21b for the PW light source 19. The drivers 21a and 21b may be controlled independently from one another, although they may be operated to selectively turn ON the respective sources at different times and/or simultaneously with one another. GI driver 21a controls the intensity, duration, and other characteristics (e.g., frequency of variation of output intensity) of the GI light generated from the GI light source 17. If the source 17 produces light for general illumination of different color characteristics, e.g. tunable white, the driver 21a may also adjust source 17 to deliver different color light. The PW driver 21b controls the intensity, duration, and other characteristics (e.g., ON/OFF frequency of variation of output intensity) of the PW light generated from the PW light source 19. Drivers 21a and 21b may be controlled by the microcontroller 22, timers, and/or by a user input. Driver 21b is configured to control the intensity and the duration of PW light output from the PW light source 19 so as to reasonably expect to produce the particular emission.

The aperture 20 may serve as the final output of the lighting device 10. In the example, the device includes a secondary optic. Although various secondary optics may be used, such as lenses, diffusers, filters or the like, the example utilizes a deflector to effectively direct the light output from the aperture 20 over a desired field of illumination. The deflector may have other shapes or be formed in other ways, but in the example, the deflector is formed by conical reflector 25.

The conical reflector 25 may have a variety of different shapes, depending on the particular lighting application. In the example, where cavity 11 is hemispherical, the cross-section of the conical reflector is typically circular. However, the reflector may be somewhat oval in shape. In applications using a semi-cylindrical cavity, the reflector may be elongated or even rectangular in cross-section. The shape of the aperture 20 also may vary, but will typically match the shape of the small end opening of the reflector 25. Hence, in the example, the aperture 20 would be circular. However, for a device with a semi-cylindrical cavity and a reflector with a rectangular cross-section, the aperture may be rectangular.

Control of the intensity, duration and other characteristics of the PW light output from the PW light source 19 ensures that the particular emission from a subject different from emissions produced by exposure of the subject to GI light is produced and will most likely be sufficient for the machine vision related detection (absent unrelated interfering circumstances). The intensity and the duration of the PW light output may be predetermined in the lighting device 10, or may be controlled (e.g., via driver 21b, microcontroller 22, user input, etc.) independently of control of the GI light output, so as to be reasonably expected to produce the particular emission in a desired place and time. When PW lighting is provided for a particular emission, the wavelength(s) for producing the particular emission are output at the intensity and having any other characteristics appropriate to the particular emission. If both GI and PW light output are provided simultaneously, and there is a spectral overlap of the GI light and the PW light, the controller may adjust the characteristics of either one or both types of light output accordingly, e.g. so that the combined light provides the characteristics at the PW wavelength(s) for the particular emission while maintaining as much as possible desirable lighting characteristics for GI purposes.

As an example, the lighting device 10 of system 1 may be oriented to output light (e.g., the combined GI light and PW light) to a space 26 that includes a subject 28 in the space. Upon exposure of the subject 28 to both the GI light and the PW light, an emission 29a from the subject 28 may be produced by exposure to the GI light and an emission 29b from the subject 28 may be produced by exposure to the PW light, where the emission 29b is other than the emission 29a. As shown by way of example, the subject 28 appears gray due to exposure to the GI light, such that the emission 29a may be a combinations of wavelengths that appear as gray (or other visible color) visible light to a person in the space. However, the emission 29b due to exposure to the PW light may be other than a wavelengths of the gray visible light, such as other visible light, infrared light, ultraviolet light, etc.

The emission 29b may be indicative of a characteristic of the subject that is detected by the machine 30. For example, the particular wavelength may produce an emission 29b that is characteristic of the chemical or physical structure of the subject 28 (e.g., blood, particular phosphor, etc.). The emission 29b may depict the location and/or shape of the subject. Additionally, the emission 29b can be based on a characteristic of the subject 28 due to exposure to GI light. The subject 28, as a characteristic, may produce an emission 29a of blue light due to exposure to the GI light. The particular wavelength PW can cause the subject to produce a particular emission 29b different from the blue light emission produced by exposure of the subject to the GI light, and the particular wavelength output to produce the particular emission is chosen based on the characteristic of the subject 28 to produce blue emissions from exposure to GI light. For example, the particular wavelength output by the lighting device can produce an emission 29b of ultraviolet light from subjects in the space 26 that produce relatively steady blue light emissions due to exposure to GI light, such that the machine vision of a machine can be configured to detect subjects that are blue based on detecting ultraviolet particular emissions from the blue subjects produced by exposure of the blue subjects to the particular wavelength.

As another example, the subject may be paint on a surface of the space 26 that produces a yellow light emission due to exposure to GI light as a characteristic, while the rest of the surface produces a white light emission due to exposure to GI light. In this later example, the particular wavelength is output and is of sufficient intensity reasonably expected to produce a white emission (e.g., a particular emission) from the paint, thereby giving the paint a similar visual appearance as the rest of the surface. This, in effect, creates a metamer between the paint and the rest of the surface. Exposure to GI light produces a white emission of the surface and a yellow emission of the paint. Based on the yellow emission produced, the particular wavelength output by the lighting device combined with the yellow emission produces a white particular emission from the paint similar to the white emission of the surface (which is different from the yellow emission produced by exposure of the paint to the GI light), thereby making the surface and the paint a metamer for a human (e.g., a white emission of the surface is produced based on exposure to GI light, and a similar apparent white emission of the paint is produced based on the combination of the yellow emission and the output of the particular wavelength, though the emission spectra of the paint and the surface may be different). The machine vision of a machine can be configured such that the created metamer for a human is not a metamer for the machine. In such an example, the vision of the machine detects the location of the paint on the surface by detecting the color difference between the paint and the surface. Alternatively, the vision of the machine may be configured to detect the particular emission from the paint and/or by filtering the particular emission from the paint.

The above described examples of subject characteristics and emissions are exemplary and not exclusive. It will be understood that a variety of subject characteristics can be exploited, and particular emissions from subjects by exposure to PW light can be produced and sensed with the systems disclosed herein for machine vision applications.

The disclosed example of a machine vision system additionally includes a machine 30. Examples of such a machine 30 may include a variety of types of apparatuses that can be configured to operate based on information obtained by the image capture device 32 and the machine vision processing system 34. The machines 30 may also include a machine controller 36 for operating the machine 30 independently from the control operations of the lighting device 10 (e.g., independent of drivers 21a, 21b, microcontroller 22, etc.). By way of just a few examples, the controller 36 may control movement of the machine 30 about the space, movement of a portion of the machine 30 (e.g. a robotic arm), control a display of the machine, trigger and alert or alarm function of the machine, etc.

The machine 30 may be used for machine vision applications. Machine vision, as can be used in the systems disclosed herein, utilizes components of a machine to detect a characteristic of a subject to control a machine function. The machine detection is supported by the output of a particular wavelength from a lighting device. The machine 30, for example, performs an operation based on detecting a characteristic of the subject 28 by processing, with a machine vision processing system 34, input that includes the particular emission from the subject 28 produced by a particular wavelength output by the lighting device 10 and that is received from an image capture device 32 coupled to the machine vision processing system 34. In the example, the machine 30 also includes a machine controller 36 that operates the machine 30 independent from the controllers that operate the lighting device 10. Examples of machine operation include movement control, detection control, function control, display control and/or other controls that may be based on detection of the characteristic of the subject in the space. Other examples of machine operation can include taking wheel alignment measurements of a car, controlling a robotic welder on a production line, detecting subjects at a particular locations, (e.g. on a production line for a relevant 'pick-and-place' robotic arm operation), detecting a user or part of a user' body extending into a dangerous zone about a machine, determining parameters from an image to determine where to steer a robot or how to further mill a part on which a milling machine is working, etc.

As an example, the machine 30 may be an object detection device that is configured to detect specific subjects based on the characteristics of the subjects and provide related information to a user of the machine. Characteristics of a subject can include subject location in a space, subject presence in a space, chemical or physical composition of the subject, etc. For example, a machine may be a visor with a display visible to a person equipped with the visor. An image capture device (e.g., a camera) on or associated with the visor is coupled to the display and configured to capture reflections of PWs or PW responsive emission in a space. A lighting device (such as lighting device 10) illuminates the space. The GI light is output for normal white lighting of the space. The PW that is output is a wavelength that, when a subject in the space (e.g., blood, DNA, contaminants, seminal fluid, etc.) is exposed to it, causes the subject 28 to emit light (e.g., infrared, ultraviolet, etc.) at a known wavelength based on a characteristic of the subject 28. For example, for preliminary blood detection, UV light may be used. The UV light causes certain other materials to fluoresce in the visible range, while the blood absorbs the UV light. Thus, the blood would appear dark on a brighter background. In such examples, the intensity of the PW light may be increased to increase the contrast between the blood and the background, aiding the machine vision to detect the blood via the image capture device and/or filters. The camera in the visor can be tuned to take images of the space, including capturing the known wavelength emitted by the subject 28 when exposed to the PW light. The images are then processed (e.g., by a processor or the like acting as the machine vision processing system 34), and the machine (e.g., a display function of the visor) is operated (e.g., by the processor or another element acting as the machine controller 36) to alter the images, making the known wavelengths emitted from the subjects in the image appear yellow (or other visible color), and then to output the altered image to the display. In this way, the visor can communicate the location of the subject to the user of the visor. The machine may also be configured to display the subject in a flashing pattern of visible light.

Other examples of machines include robotic machines constructed for production or movement. For example, robotic devices that are constructed for movement through a space can be designed to move based on grid guidance patterns applied to the space. Such machines can be configured to detect the characteristics of the grid guidance patterns based on particular emissions produced by the PW light utilizing machine vision. In the above described example of utilizing paint of a known characteristic, a grid pattern in a space formed with the paint can be visibly hidden by producing a particular emission from the paint so as to make the paint appear similar to the rest of the space. In such an example, a machine using machine vision can be configured to detect the particular emission of the paint and/or filter the detected particular emission, thereby causing the machine to detect the location of the grid pattern, and operate so as to move the machine along the grid pattern. Such machines can also be configured to restrict movement based on detecting the location of obstructions in a space utilizing the disclosed systems. For example, the machine can be configured to interact with or avoid interacting with subjects in a space that emit a particular color of light when exposed to GI light.

Machines for machine vision using the PW lighting can also include machines configured to scan a subject and capture information from the subject based on a particular emission from the subject. In one such example, the subject is text printed with ink of which light of a particular wavelength produces a particular emission from the text, allowing the machine with appropriately configured machine vision components to detect the location of the text (e.g., the characteristic of the text). Upon detecting the location of the text, the machine can be configured to perform a scanning and recording operation of the text, for example, via image capture. Similar techniques may be used to detect other types of printed symbols or indicia, e.g. bar codes or holographic images.

Additional examples of machines for machine vision include security systems configured to detect particular emissions from metals, residues, and the like based on corresponding characteristics that cause a particular emission of the metals/residues to be produced by exposure to PW light. Such machines may be configured to alert of the presence of a subject with a particular characteristic based on lighting contrast differences. For example, a lighting system may be configured to produce a particular emission of a subject that is of a visible wavelength. It may be desirable in such examples to mask the visibility of the particular emission (e.g., in security applications). The color temperature/contrast of GI light output from the lighting device can be increased to mask the appearance of the particular emission. The machine can be configured to capture and process images for contrast correction, detect the characteristic of the subject, and operate to provide an alert as to the detection of the characteristic of the subject.

It will be understood that a variety of machines and machine vision applications can be utilized with and can benefit from the disclosed systems herein in addition to those machines and machine vision applications described above.

As illustrated FIG. 1, the machine 30 includes an image capture device 32, a machine vision processing system 34, and a machine controller 36. The image capture device 32 as shown is coupled to the machine vision system 34. Although depicted integrated into the machine 30, the image capture device 32 may be in communication with the machine 30 externally. For example, the image capture device 32 may be integrated into the lighting device 10, the space 26, etc., and in wireless communication (e.g., WiFi, BlueTooth, NFC, etc.) with the machine 30 and/or the machine vision processing system 34. The image capture device 32 is configured to image the space 26 and/or subjects in the space and configured to send the image(s) to the machine vision processing system 34 as an input for the machine vision processing system 34. The image capture device 32 may be a detector, camera, CCD, and/or other suitable devices for capturing images. More than one image capturing device may be utilized in the disclosed systems (e.g., multiple image capturing devices for multiple spaces and/or 3-D imaging). For example, the image capture device 32 may be tuned to the particular wavelength or wavelengths output from PW source 19 (e.g. to detect emissions from the subject 28 under the particular illumination) or to detect an emission from the subject 28 when exposed to the particular wavelength(s). As an example, the subject may be blood, and a particular wavelength may be emitted at a sufficient intensity reasonably expected to produce a particular emission from the subject based on the characteristic of blood. The image capture device 32 can be configured to capture the particular emission expected to be produced by exposure of the subject to the particular wavelength.

The machines in the disclosed examples also include a machine vision processing system (MVPS) 34. The MVPS 34 is coupled to the image capture device 32 and is configured to receive captured images from the image capture device 32 as an input for processing. The MVPS 34 is configured to process the input received from the image capture device 32 and to detect a characteristic of the subject in the space in response to receiving the input. The MVPS 34 benefits from the particular wavelength output by the lighting device 10 for the detection of the characteristic of the subject in that the outputted wavelength(s) causes emission from a subject of light of a particular characteristic that allows the MVPS 34 to perform the appropriate image processing for the machine vision application. Instead of or in addition to the tuning of the image capture device 32 outlined above, the MVPS 34 may be tuned to the particular wavelength and/or the particular emission reasonably expected to be produced by exposure of the subject to the particular wavelength. As an example with the paint described above, the MVPS 34 can be configured to detect the characteristic of the paint by processing the input from the image capture device 32 to detect the particular emissions of the paint due to exposure to the particular wavelength. As another example, the MVPS 34 can be configured to detect the characteristic of the subject by filtering the particular emissions captured by the image capture device 32. In such examples, the MVPS 34 can cause the machine 30 to view the subject as though the subject is only exposed to the GI light and not the PW light, as the MVPS 34 (or other component of the machine vision system) filters the particular emissions produced by exposure to PW light.

In some examples, the machine 30 uses filters for machine vision applications. A filter may be coupled with the image capture device 32, the MVPS 34, and/or the lighting device 10. For example, a filter may be placed over the image capture device 32 and may be configured to exclude, alter, and/or enhance particular emissions in captured images to be used by the MVPS 34 for operation of the machine 30. In another example, the filter is coupled to the MVPS 34 for hyperspectral imaging. The MVPS 34 may include a time based filter that is calibrated to an output rate of the particular emission. For example, the PW light is output at a predetermined frequency, and the filter is calibrated to the predetermined frequency. In another example, a filter is coupled to the lighting device and is configured to selectively permit predetermined wavelengths to be output from the lighting device. It is contemplated that any combination of filters described herein may be used in the disclosed machine vision systems.

Examples of machines of the disclosed systems can also be configured to operate via a machine controller 36 that is coupled to the image capture device 32 and the MVPS 34. The controller 36 may be coupled to other components of the machine 30 not shown, such as wheels, displays, appendages, etc. The controller 36 operates the machine 30 based, at least in part, on the detection of the characteristic of the subject. Additionally, the controller 36 may operate the machine 30 independently and separately from the controllers of the lighting device 10 (e.g., drivers 21*a*, 21*b*, microcontroller 22, etc.) and/or other components of the system 1. Although shown as independently operating devices, the controller 22 of the lighting device 10 and the image capture device 32 and/or processing system 34 of the machine 30 may be operationally linked if appropriate. For example, timing of PW output by the source 19 in device 10 may be coordinated with operations of the image capture device 32 in machine 30.

The MVPS 34 may operate to communicate the location of the subject in the space based on detecting the characteristic of the subject from the input. As another example, the MVPS 34 and/or controller 36 operates the machine to control movement of the machine 30 through the space based on the detected characteristics. In such examples, the subject may be a grid movement guidance pattern, e.g. on the floor or other appropriate surface(s) in the space 26. The MVPS 34 is configured to detect the characteristic(s) of the grid pattern; and, based on the detected characteristics, the MVPS 34 and/or controller 36 controls the movement of the machine 30 through the space based on the grid guidance pattern. In addition to grids, the subject may also define a movement perimeter or movement boundaries in the space that the MVPS 34 is configured to detect and the controller 36 is configured to operate movement of the machine 30 according to the movement perimeter or movement boundaries. The controller 36 may also be operable to communicate a chemical or physical property of the subject based on the detected characteristic. For example, the MVPS 34 can be configured to detect multiple types of subjects within the space (e.g., blood and contaminants), such that the machine 30, via the controller 36, operates to communicate the type of subject in the space based on the detected characteristic. It will be recognized that the above described machine operations that can be based, at least in part, on the detected characteristic of a subject in a space are exemplary and not exclusive, as many operational functions for machines can be accomplished with the systems disclosed herein.

Figure 2:
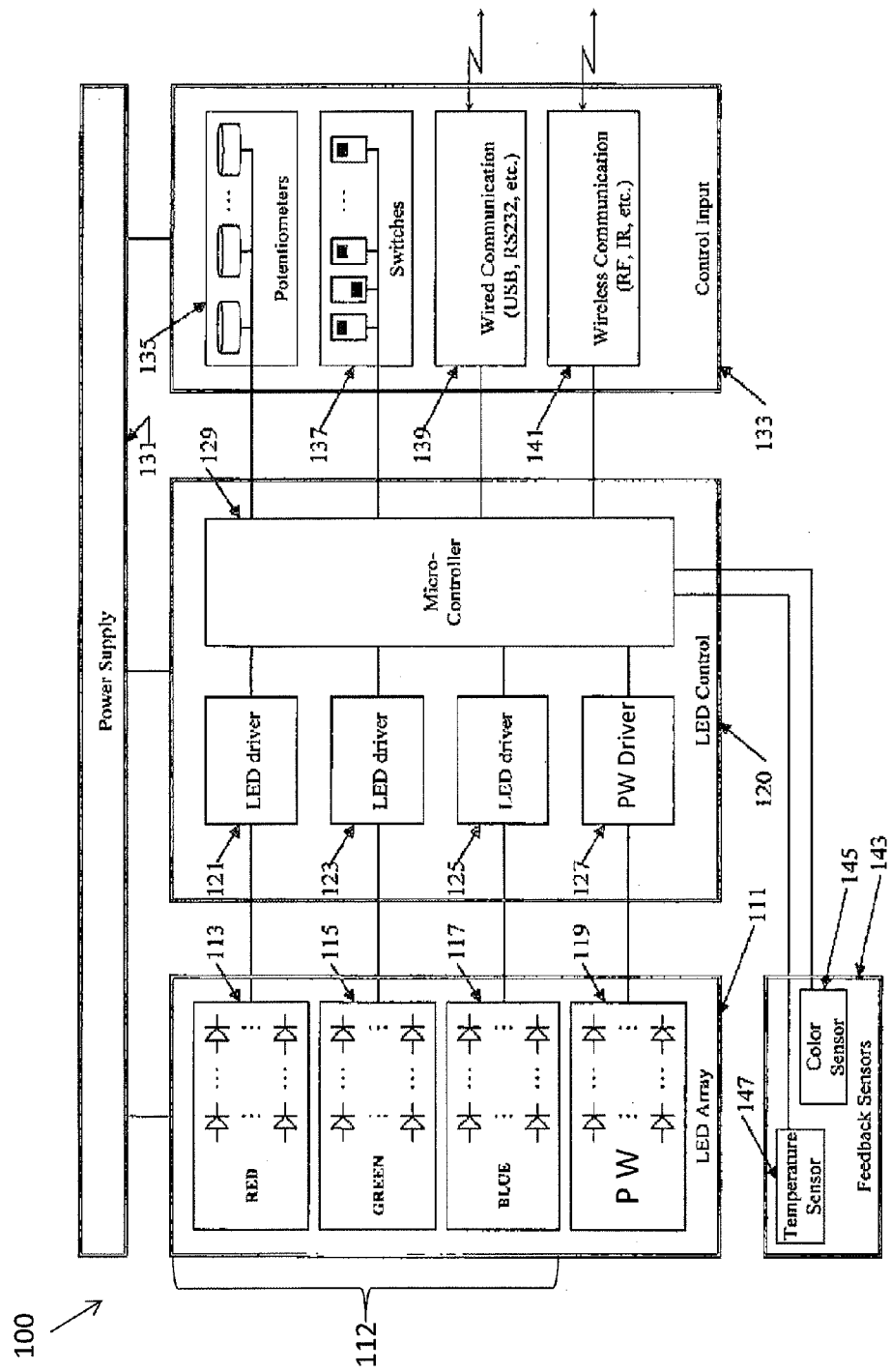
FIG. 2 is a functional block diagram of electrical components of a lighting device for generating general illumination light and for generating particular wavelengths that produce emissions different from emissions produced by exposure to the general illumination.

FIG. 2 is a block diagram of exemplary circuitry for the sources and associated control circuit, providing digital programmable control, which may be utilized with the systems and lighting devices of the type described above. In this circuit example, the sources of radiant energy of the various types together form an LED array 111. Although white LEDs or combinations of white and other colors of LEDs may be used as a general illumination light source 112, the example uses LEDs of several different colors to provide the general illumination. Hence, array 111 comprises two or more LEDs of each of the three primary colors, red green and blue, represented by LED blocks 113, 115 and 117. For example, the array may comprise six red LEDs 113, three green LEDs 115 and three blue LEDs 117. The LED blocks 113, 115, and 117 make up the light source 112 for general illumination (e.g., GI light) of a space.

The LED array in this example also includes a number of additional or "other" LEDs 119 that make up the light source for generating light of a particular wavelength (e.g., PW light). There are several types of additional LEDs that are of particular interest in the present discussion. One type of additional LED provides one or more additional wavelengths of radiant energy for each beneficial purpose to be supported by operation of the device 10, for integration within the cavity 11. The additional wavelengths may be in the visible portion of the light spectrum. Alternatively, the additional wavelength LEDs may provide energy in one or more wavelengths outside the visible spectrum, for example, in the infrared range or the ultraviolet range. The additional wavelengths generated by the PW light source 119 are particular and are of a sufficient intensity and duration to produce a particular emission from a subject different than an emission produced by exposure of the subject to GI light.

Another type of alternative or additional LED of interest is a white LED. For white lighting applications, one or more white LEDs provide increased intensity. The primary color LEDs then provide light for color adjustment and/or correction of the GI light generated by the GI light source 112. The white LED may also be used for adjustment and/or correction of the PW light generated by the PW light source 119.

The electrical components shown in FIG. 2 also include an LED control system 120. The system 120 includes driver circuits for the various LEDs and a microcontroller. The driver circuits supply electrical current to the respective LEDs 113 to 119 to cause the LEDs to emit light. The driver circuit 121 drives the red LEDs 113, the driver circuit 123 drives the green LEDs 115, and the driver circuit 125 drives the blue LEDs 117. In this example using three types of LEDs to implement the GI source, the driver circuits 121, 123, and 125 make up the general illumination driver (GI driver) for the GI light source 112. In a similar fashion, when active, the particular wavelength driver circuit (PW driver) 127 provides electrical current to the PW LEDs 119. If the other LEDs provide another color of light, and are connected in series, there may be a single driver circuit 127. The intensity of the outputted light of a given LED is related to the level of current supplied by the respective driver circuit. As such, the PW driver 127 is configured to supply sufficient current to the PW light source 119 such that the particular emission can be produced by exposure to the PW light.

The current output of each driver circuit is controlled by the higher level logic of the system. In this digital control example, that logic is implemented by a programmable microcontroller 129, although those skilled in the art will recognize that the logic could take other forms, such as discrete logic components, an application specific integrated circuit (ASIC), etc.

The LED driver circuits and the microcontroller 129 receive power from a power supply 131, which is connected to an appropriate power source (not separately shown). For most task-lighting applications, the power source will be an AC line current source, however, some applications may utilize DC power from a battery or the like. The power supply 129 converts the voltage and current from the source to the levels needed by the driver circuits 121-127 and the microcontroller 129.

A programmable microcontroller typically includes or has coupled thereto random-access memory (RAM) for storing data and read-only memory (ROM) and/or electrically erasable read only memory (EEROM) for storing control programming and any pre-defined operational parameters, such as pre-established light 'recipes.' The microcontroller 129 itself comprises registers and other components for implementing a central processing unit (CPU) and possibly an associated arithmetic logic unit. The CPU implements the program to process data in the desired manner and thereby generate desired control outputs.

The microcontroller 129 is programmed to control the LED driver circuits 121-125 to set the individual output intensities of the LEDs 113-117 to desired levels, so that the light generated from the GI light source 112 from the aperture of the cavity has a desired spectral characteristic and a desired overall intensity. The microcontroller 129 is also programmed to control the PW driver 127 independently from and/or simultaneously to the GI drivers 121-125, such that the PW light generated by LEDs 119 is of a sufficient intensity, is output for a sufficient duration, and/or has the appropriate characteristics so as to produce a particular emission of the subject. The microcontroller 129 may be programmed to essentially establish and maintain or preset a desired 'recipe' or mixture of the available wavelengths provided by the LEDs used in the particular system, at different times or under different conditions and/or for different operational purposes. For example, there may be one or several such recipes for general lighting and one or more for each particular wavelength lighting purpose supported by the particular implementation of the lighting device. The microcontroller 129 receives control inputs specifying the particular 'recipe' or mixture, as will be discussed below. To insure that the desired mixture is maintained for the GI light, the microcontroller may receive a color feedback signal from an appropriate color sensor. The microcontroller may also be responsive to a feedback signal from a temperature sensor, for example, in or near the optical integrating cavity.

The electrical system will also include one or more control inputs 133 for inputting information instructing the microcontroller 129 as to the desired operational settings. A number of different types of inputs may be used, and several alternatives are illustrated for convenience. A given installation may include a selected one or more of the illustrated (or other) control input mechanisms.

As one example, user inputs take the form of a number of potentiometers 135. The number would typically correspond to the number of different light wavelengths provided by the GI light source 112 and the particular wavelength provided by the PW light source 119. The potentiometers 135 typically connect through one or more analog to digital conversion interfaces provided by the microcontroller 129 (or in associated circuitry). To set the parameters for the GI light, the user adjusts the potentiometers 135 to set the intensity for each color in the GI light source 112. Correspondingly, a user may adjust the potentiometers 135 to activate the PW light source 119, and/or to set the desired intensity, duration, and characteristic of the PW light to produce the particular emission from the subject in the space. The microcontroller 129 senses the input settings and controls the LED driver circuits accordingly to set corresponding intensity levels for the LEDs providing the light for general illumination and the light of the particular wavelength.

Another user input implementation might utilize one or more dip switches 137. For example, there might be a series of such switches to input a code corresponding to one of a number of recipes. The memory used by the microcontroller 129 would store the necessary intensity levels for the different color LEDs in the GI light source 112 for each recipe. Based on the input code, the microcontroller 129 retrieves the appropriate recipe from memory. Then, the microcontroller 129 controls the GI LED driver circuits 121-125 accordingly, to set corresponding intensity levels for the LEDs 113-117 providing the light for general illumination of the space. The microcontroller 129 may operate similarly for independent activation and control of the PW light source 119 and the PW driver 127 to generate light of the particular wavelength.

As an alternative or in addition to the user input in the form of potentiometers 135 or dip switches 137, the microcontroller 129 may be responsive to control data supplied from a separate source or a remote source. For that purpose, some versions of the system will include one or more communication interfaces. One example of a general class of such interfaces is a wired interface 139. One type of wired interface typically enables communications to and/or from a personal computer or the like, typically within the premises in which the fixture operates. Examples of such local wired interfaces include USB, RS-232, and wire-type local area network (LAN) interfaces. Other wired interfaces, such as appropriate modems, might enable cable or telephone line communications with a remote computer, typically outside the premises. Other examples of data interfaces provide wireless communications, as represented by the interface 141 in FIG. 2. Wireless interfaces, for example, use radio frequency (RF) or infrared (IR) links. The wireless communications may be local on-premises communications, analogous to a wireless local area network (WLAN). Alternatively, the wireless communications may enable communication with a remote device outside the premises, using wireless links to a wide area network.

As noted above, the electrical components may also include one or more feedback sensors 143, to provide system performance measurements as feedback signals to the control logic, implemented in this example by the microcontroller 129. A variety of different sensors may be used, alone or in combination, for different applications. In the illustrated examples, the set 143 of feedback sensors includes a color sensor 145 and a temperature sensor 147. Although not shown, other feedback sensors, such as an overall intensity sensor may be used. Alternatively or in addition, the system may include external condition sensors, for example, to sense ambient light level and/or color characteristics or to sense occupancy. The feedback and/or external condition sensors are positioned in or around the system to measure the appropriate physical condition, e.g. temperature, color, intensity, etc.

The color feedback sensor 145, for example, is coupled to detect color distribution in the integrated radiant energy. The color sensor may be coupled to sense energy within the optical integrating cavity, within the deflector (if provided) or at a point in the field illuminated by the particular system. Various examples of appropriate color sensors are known. If mainly used for feedback sensing relative to the general lighting illumination, the sensor 145 might be an RGB color sensor such as a Hamamatsu style RGB color sensor. Another suitable sensor might use the quadrant light detector disclosed in U.S. Pat. No. 5,877,490, with appropriate color separation on the various light detector elements (see U.S. Pat. No. 5,914,487 for discussion of the color analysis). Alternative or additional sensors may be provided for sensing light in one or more wavelength ranges from the PW LEDs 119.

The associated logic circuitry, responsive to the detected color distribution, controls the output intensity of the GI light and controls the PW light independently from the GI light, so as to provide a desired color distribution in the integrated radiant energy for general illumination of the space, as well as particular wavelengths of sufficient intensity, duration, and characteristic for producing a particular emission from a subject different from an emission produced by general illumination of the space, in accord with appropriate settings. The color sensor measures the color of the integrated radiant energy produced by the system and provides a color measurement signal to the microcontroller 129.

The temperature sensor 147 may be a simple thermoelectric transducer with an associated analog to digital converter, or a variety of other temperature detectors may be used. The temperature sensor is positioned on or inside of the fixture, typically at a point that is near the LEDs or other sources that produce most of the system heat. The temperature sensor 147 provides a signal representing the measured temperature to the microcontroller 129. The system logic, here implemented by the microcontroller 129, can adjust intensity of one or more of the LEDs in response to the sensed temperature, e.g. to reduce intensity of the source outputs to compensate for temperature increases.

The systems and methods disclosed herein include a lighting system to generate light for general illumination of a space and generate light of a particular wavelength of a sufficient intensity, duration, and characteristic reasonably expected to produce a particular emission from a subject in a space different from an emission produced by exposure of the subject to general illumination. The general illumination light and the light of the particular wavelength can be generated independently of each other. In an example, the particular wavelength (PW) light is generated from a discrete light source separate from the light source for generating general illumination (GI) light, and both sources are integrated into the same lighting device.

Subjects in a space that are illuminated by the lighting devices have optical characteristics that respond under exposure to light. Exposure to GI light produces an emission from a subject in a space. For example, blue ink will emit blue light under exposure to general illumination light. When the optical properties of a subject are known, particular wavelengths can be output at sufficient intensities reasonably expected to produce a particular emission from the subject different than an emission produced by exposure of the subject to GI light. As an example, the same blue ink can be exposed to PW light of sufficient intensity and duration reasonably expected to produce violet light as a particular emission from the subject. In such an example, the particular emission may be visible without the use of a detector/image capture device. Alternatively, the subject can be exposed to PW light that produces a particular emission outside the visible spectrum, which would require a detector (e.g., an image capture device, filter, machine vision processing system, etc.) configured to detect such a particular emission.

A subject in the space may also be visibly disguised by use of PW light producing a particular emission from the subject. For example, paint may be applied to the floor of a space and exposure to GI light produces an emission of yellow light of the paint, while the GI light produces a white emission from the rest of the floor. If the optical properties of the paint are known (e.g., the emission curves and excitation curves), simultaneously outputting PW light of a sufficient intensity and/or parameter in combination with the yellow light emission from the paint can produce a particular emission of white light from the paint, which would cause the paint to appear visibly similar to the floor. An image capture device in a machine vision application, such as a camera, could be used to detect and/or filter the particular emission of the paint, and then a processor, such as a machine vision processing system, can filter the particular emission, such that the location of the paint is detected.

Subjects in the space can include various types of subject of which optical properties are known such that exposure to PW light produces a particular emission from the subject different from an emission produced by exposure of the subject to GI light. Examples of subjects include furniture, fixtures, paints, blood, dust, contaminants, explosives residue, liquids, obstructions, etc., contained with a space. The above list of objects is exemplary and not exclusive, as it is contemplated a variety of subjects can be utilized in the disclosed systems of which the optical properties of the subjects are known.

In examples of the systems disclosed herein, machines can be constructed to operate based on detected characteristics of the subjects supported by the PW light output from the lighting devices. The machines can include image capturing devices that image the space with the subject(s), and the image capture devices can be tuned or configured specifically for use with the particular wavelength to capture the particular emissions of the subjects and the characteristics of the subjects. The machines may implement machine vision processing systems that receive the images from the input capturing devices as an input to detect the characteristics of the subjects in the space. The detected characteristics of the subject can include location of the subject, position of the subject, chemical and/or physical properties of the subject, type of subject, and other characteristics that a machine can detect for operation of the machine based, at least in part, on the detected characteristics. The machine may be operated with a machine controller coupled to the machine vision processing system and configured to operate the machine independent of other controllers within the system. The operation may be movement operation such that the location of the subject is used by the machine to determine where the machine can move within the space. The type of subject may be a movement guidance pattern, such as a grid pattern, that the machine uses to operate movement within the space. The chemical or physical properties of the subject can be blood type or contaminant type, and the operation of the machine can be communication of the property of the subject. A variety of machine operations in addition to those described above may be performed based on the detection of a characteristic of a subject in a space with the systems disclosed herein.

Figure 3:
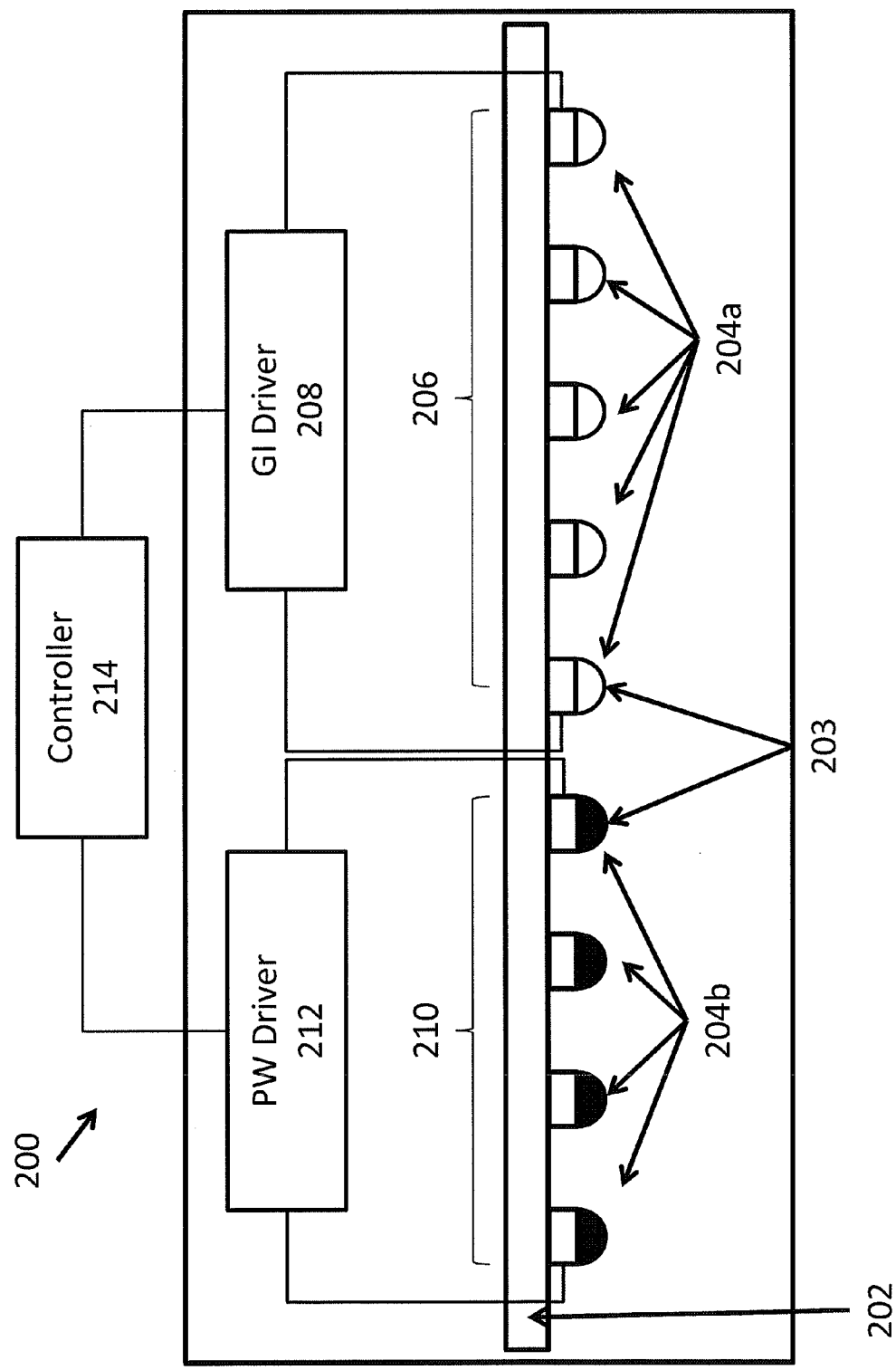
FIG. 3 is a diagram showing an example of a lighting device for generating particular wavelengths with a dimming mechanism.
Figure 4:
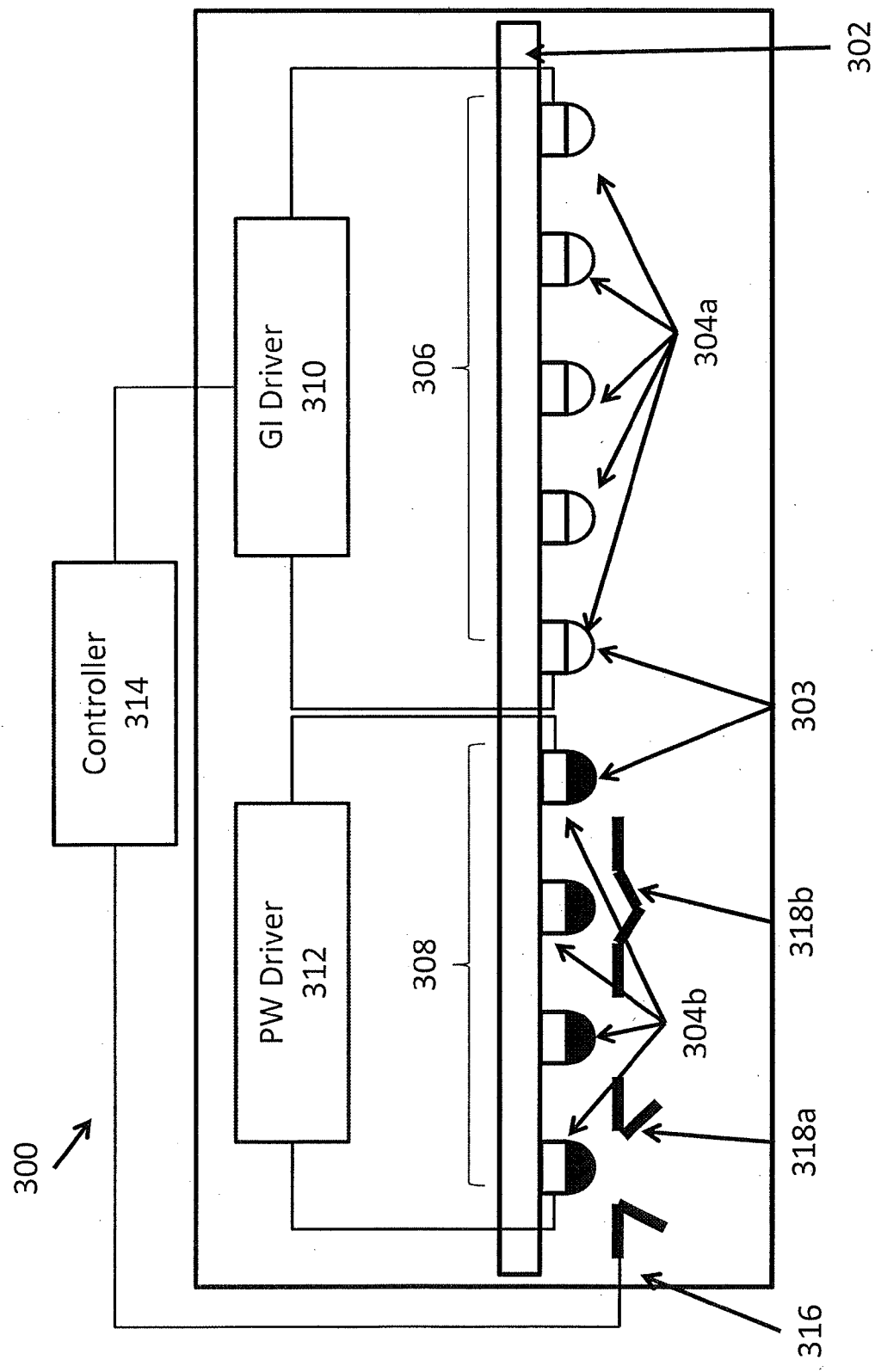
FIG. 4 is a diagram showing an example of a lighting device for generating particular wavelengths with shutter mechanisms.
Figure 5:
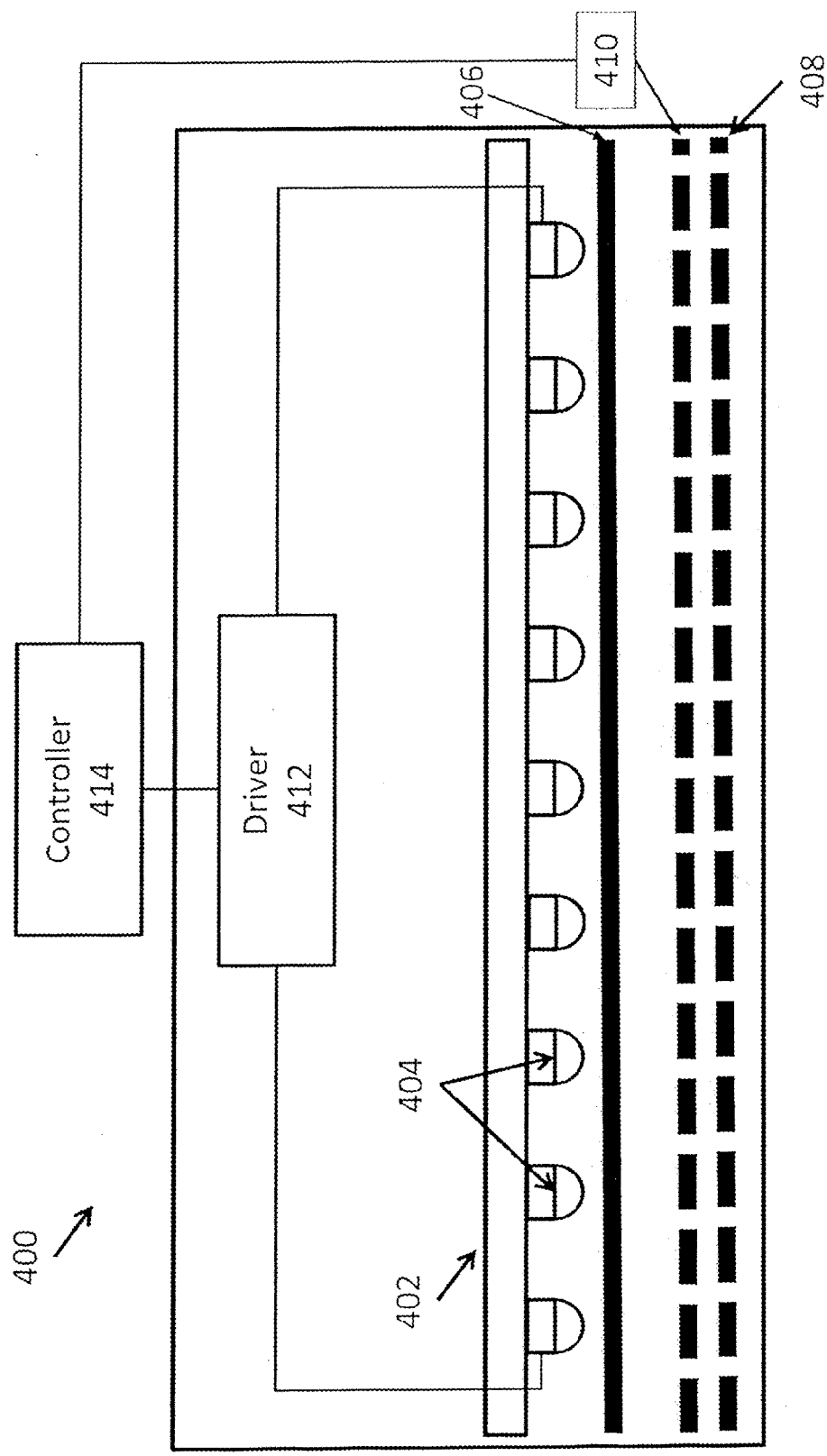
FIG. 5 is a diagram showing an example of a lighting device for generating particular wavelengths with a pixelated screen and an LCD shutter array.

Additional examples of mechanisms for producing light for general illumination and particular wavelengths with the lighting devices for use in machine vision applications of the disclosed systems are depicted in FIGS. 3-5. For convenience of illustration, these illustrations show examples of lighting devices positioned to emit light downward, e.g. from a ceiling fixture or drop-light type installation. As with the earlier examples, the examples in FIGS. 3-5 may be positioned or oriented to output light in other directions as suitable for particular lighting applications and/or installations.

FIG. 3 shows an example of a lighting device utilizing a dimming mechanism. The lighting system 200 includes an array 202 of LEDs 203. The array 202 is partitioned into a general illumination (GI) section 206 coupled to a general illumination (GI) driver 208 and a particular wavelength (PW) section 210 coupled to a particular wavelength (PW) driver 212. The GI section 206 functions as the GI light source and the PW section 210 functions as the PW light source for the lighting device 200. A controller 214 is coupled to the GI driver 208 and the PW driver 212 and the drivers 210 and 212 operate in response to the controller 214. The controller 214 operates the PW driver 212 independently from and/or simultaneously to the GI driver 208. The controller 214 may operate the drivers 210 and 212 based on predetermined settings, timers, and/or user input. The drivers and controller may be implemented in a manner similar to the drivers and controllers in the earlier examples. For convenience, the optical elements coupled to the sources so as to supply both types of light to the device output are not shown specifically in this drawing.

The LEDs 204a on the GI section 206 produce light for general illumination of a space, and may be configured and arranged to produce fixed white light, tunable white light, RGB, etc. The LEDs 204b on the PW section 206 generate light of a particular wavelength to produce a particular emission from a subject different from an emission produced by exposure of the subject to GI light. In the example illustrated in FIG. 3, the PW driver 212 implements a dimming mechanism such that, in response to a corresponding signal from the controller 214, the PW driver 212 decreases the brightness and intensity of the PW LEDs 204b independently from the GI LEDs 204a when the output of the PW is not desired. The brightness and intensity of the GI LEDs 204a can be maintained and, thus, GI light is output, illuminating the space. When the output of the PW light is desired, the PW driver 212, in response to a corresponding signal from the controller 214, increases the brightness and intensity of the PW LEDs 204b to a sufficient level, and the intensity of the PW LEDs 204b is maintained for a sufficient duration reasonably expected to produce the particular emission from the subject. When the output of the PW is desired and the intensity of the PW LEDs 204b is increased, the brightness and intensity of the GI LEDs 204a may be independently maintained, such that both general illumination of the space and the output of PWs to produce the particular emission is accomplished. In such examples, the light generated by the PW section 208 may have little effect on the appearance of the light generated by the GI section 206. The GI driver 210 may also include a dimming mechanism to adjust the brightness of the GI LEDs 204a independently from the PW LEDs 204b and/or a switch to power the GI LEDs 204a ON or OFF independently from the PW LEDs 204b. Thus, it is contemplated that the lighting devices disclosed, such as lighting system 200, may be operable to generate PW light while not generating GI light, and vice versa.

FIG. 4 depicts another example of a lighting device. The lighting system 300 includes an array 302 of LEDs 303. The array 302 of LEDs 303 is partitioned into a GI section 306 and a PW section 308. A GI driver 310 is coupled to the GI section 306 and a PW driver 312 is coupled to the PW section 308. A controller 314 is coupled to the GI driver 310. The controller 314 may function with respect to GI driver 310 as the controller 214 functions with respect to GI driver 210 described above with regard to FIG. 3. The drivers and controller may also be implemented in a manner similar to the drivers and controllers in the other earlier examples. For convenience, the optical elements coupled to the sources so as to supply both types of light to the device output are not shown specifically in this drawing.

In this example, the controller 314 is also coupled to an array of shutters 316 that are positioned between the PW LEDs 304b and the output (not shown) of the lighting device 300. The shutters 316 may be mechanical shutters, LCD shutters, microelectromechanical (MEM) shutters, etc. Shutter 318a is shown in an open position, allowing PW light generated from a PW LED to pass through the output of the lighting device 300 and be output from the lighting device 300, and shutter 318b is shown in a closed position, blocking PW light generated from a PW LED from passing through the output of the lighting device 300, therefore preventing the PW LED light from being output from the lighting device 300.

In the example depicted in FIG. 4, the PW driver 312 operates the PW LEDs 304b at a sufficient brightness and intensity so as to produce the particular emission from the subject with the PW light output by the PW LEDs 304b. The output of the PW light is regulated by the array of shutters 316 coupled to the controller 314. The shutters 316 open upon receiving a corresponding opening signal from the controller 314, thereby allowing the PW light generated at the PW section 318 to pass through the output of the lighting device 300. Shutters 316 may be controlled together in groups, or each individual one of the shutters may be separately controlled. The shutters 316 close upon receiving a corresponding closing signal(s) from the controller 314, thereby preventing the PW light from passing through the output of the lighting device 300. The controller 314 may be configured to signal a portion of the array of shutters 316 to open and/or close, which can reduce or increase the brightness and intensity of the PW light that passes through the output of the lighting device 300. In such examples, a number shutters in the array of shutters 316 will be open (e.g., open shutter 318a) and a number of shutters will be closed (e.g., closed shutter 318b).

The lighting device 300 may also include an array of similar shutters (not shown) positioned between the GI LEDs 304a and the output of the lighting device 300 that are coupled to the controller to selectively permit GI light to pass through the output. In such examples, the shutters positioned over the GI light section 306 may be controlled independently from the shutters 316 over the PW light section 308. Although not depicted, the controller 314 may be coupled to the PW driver 312 to control the brightness and intensity of the PW LEDs 304b.

It is contemplated that the lighting devices 200 and 300 (and other lighting devices disclosed herein) may incorporate a combination of dimming mechanisms as described relative to FIG. 3 along with any number or arrangement of shutters, such as shutters 316 of FIG. 4, to generate light for general illumination and to generate PW light to produce a particular emission from a subject in a space different from an emission produced by exposure of the subject to the GI light.

Additionally, more than one particular wavelength may be generated by the lighting systems. For example, the arrays 202, 302 of LEDs can be partitioned into a GI light section and multiple PW light sections, with each PW light section having an independent PW driver being capable of generating distinct PWs. Thus, the lighting devices disclosed may include a GI light source, a first PW light source for generating a first particular wavelength to produce a first particular emission from a subject, a second PW light source for generating light of a second particular wavelength to produce a second particular emission from a subject, and so on.

The examples of FIGS. 3 and 4 show the LEDs of the different types in different sections of the arrays. It should be apparent that other arrangements of the LEDs in and about each array may be used. For example, the LEDs for GI output may be dispersed at various locations about the array and the LEDs for PW output may be dispersed about the array so as to be intermingled with the LEDs for GI output.

FIG. 5 illustrates a further example of a lighting device for generating GI light and PW light with a GI light source and a PW light source integrated into the same device. The lighting system 400 includes an array 402 of lights 404 (e.g., LEDs), a polarizer 406 positioned over the lights 404, and a pixelated screen 408. The array 402 of lights 404 may operate as a light source (e.g., a back light) for projecting light toward the pixelated screen 408. The pixelated screen 408 may be a pixelated phosphorescent screen, a pixelated florescent screen, a screen implementing LEDs, phosphors, quantum dots, etc. In the example of FIG. 5, the GI light source (not finely delineated) may be a partitioned section of pixels in the screen 408 that includes pixels dedicated to generating and outputting light for general illumination or may be pixels for general illumination output at selected locations dispersed across the screen area. Additionally, the PW light source (not finely delineated) may be pixels in another partitioned section of the screen 408 or may be pixels at other selected locations dispersed across the screen area, configured to generate and output light of a particular wavelength that produce a particular emission from a subject different from an emission produced by exposure of the subject to GI light. Between the polarizer 406 and the screen 408 is an array of LCDs 410. A driver 412 is coupled to the array 402, and a controller 414 is coupled to the driver 412 and the LCDs 410. The LCDs 410 act as shutters and the device may include an LCD shutter corresponding to each pixel on the screen 408. The LCDs 410 can be configured to operate as discrete shutters (e.g., shutters with only an open and closed position), or as gray-scale shutters. The drivers and controller may be implemented in a manner similar to the drivers and controllers in the earlier examples. For convenience, the optical elements coupled to the sources so as to supply both types of light to the device output are not shown specifically in this drawing.

The pixelated screen 408 may include fluorescent materials, such as of any suitable type phosphor, e.g., traditional phosphors, doped semiconductor nanophosphors or quantum dots. Wavelength converting materials absorb excitation energy then re-emit the energy as radiation of a different wavelength than the initial excitation energy. For example, some phosphors produce a down-conversion referred to as a "Stoke shift," in which the emitted radiation has less quantum energy and thus a longer wavelength. Other phosphors produce an up-conversion or "Anti-Stokes shift," in which the emitted radiation has greater quantum energy and thus a shorter wavelength.

Semiconductor nanophosphors, sometimes referred to as Quantum dots (QDs), provide similar shifts in wavelengths of light. QDs are nano scale semiconductor particles, typically crystalline in nature, which absorb light of one wavelength and re-emit light at a different wavelength, much like conventional phosphors. However, unlike conventional phosphors, optical properties of the quantum dots can be more easily tailored, for example, as a function of the size of the dots. In this way, for example, it is possible to adjust the absorption spectrum and/or the emission spectrum of the QDs by controlling crystal formation during the manufacturing process so as to change the size of the QDs. Thus, QDs of the same material, but with different sizes, can absorb and/or emit light of different colors. For at least some exemplary QD materials, the larger the dots, the redder the spectrum of re-emitted light; whereas smaller dots produce a bluer spectrum of re-emitted light.

Doped semiconductor nanophosphors are somewhat similar in that they are nanocrystals formed of semiconductor materials. However, this later type of semiconductor nanophosphors is doped, for example, with a transition metal or a rare earth metal. For white GI light emission, mixtures may use two, three or more doped semiconductor nanophosphors and may further include one or more non-doped semiconductor nanophosphor.

Doped semiconductor nanophosphors may be used individually to generate PW emissions. Doped semiconductor nanophosphors exhibit a relatively large Stokes shift, from shorter wavelength of absorption spectra to longer wavelength emissions spectra. If desirable for a device supporting a number of different PW applications, several doped semiconductor nanophosphor types may be used that are excited in response to a particular electromagnetic energy range but where each type re-emits visible light of a different spectral characteristic. At least for the doped semiconductor nanophosphors, each phosphor emission spectra may then have little or no overlap with excitation or absorption ranges of the doped semiconductor nanophosphors dispersed in the material, so as to support spectrally separate PW emissions without substantial cross-excitation.

Utilizing the properties of the luminescent phosphor materials, each pixel in the screen 408 can be tailored to produce a particular wavelength or range of wavelengths in the spectrum. The phosphors may have different excitation spectra, and use of different phosphors might require use of LEDs emitting multiple types/colors of light to drive the phosphors. In our example, however, we will assume that all of the phosphors used in the various pixels of the screen 408 are of types having excitation spectra that overlap each other in a spectral region that includes the emission spectra of a particular type of LED. For example, the screen 408 may use nanophosphors of various types excited in response to near ultraviolet (UV) electromagnetic energy in the range of 380-420 nm and/or of various types excited in response to UV energy in a range of 380 nm and shorter. In such an example, the LEDs 402 therefore all may be of that same particular type, e.g. of a type for emission at a nominal wavelength in the range of 380-420 nm or of a type for emission at a nominal wavelength in the range of 380 nm and shorter.

When light from the LED array 402 passes through the polarizer 406, the controller 414 operates the LCD shutters 410 (either discrete or gray-scale) to selectively permit the light to pass and enter the pixels of the screen 408. The pixels, made up of phosphors or quantum dots, will generate light of a wavelength corresponding to the properties of each pixel, when the respective LCD pixels of the array 410 allow light to pass through to the phosphor pixels of screen 408 to excite output of PWs by those phosphor pixels.

With this structure, sections of the screen 408 can be partitioned such that a section includes only pixels that output a particular wavelength to produce a particular emission of a subject (e.g., a PW). Other sections of the screen 408 (or the rest of the screen 408) may include phosphor materials that emit various wavelengths which can be combined to produce light for general illumination. Thus, the lighting device 400 can utilize the LCDs 410 to prevent light generated by the array 402 from entering the sections of the screen 408 constructed for outputting the PWs, and to allow light generated by the array 402 to enter the sections of the screen 408 for outputting GI light. The LCDs 410 can be controlled to output both GI light and PWs and either GI light or PWs independent of each other.

In an additional example, the LCDs 410 may be gray-scale shutters, such that various brightness and intensities of the light from the array 402 are permitted to pass through each of the pixels in the screen 408. Controlling an LCD in the LCD array 410 toward the darker end of the gray-scale via the controller 414 sends dimmer, lower intensity light to the phosphor pixel, thus making the subsequent light output from the pixel of a lower intensity. Controlling an LCD in the LCD array 410 toward the lighter end of the gray-scale via the controller 414 sends brighter, higher intensity light to the phosphor pixel, making the subsequent light output from the pixel of a higher intensity. Utilizing a gray-scale LCD array, the intensity of a section of the screen 408 can be increased such that, if the section is composed of pixels constructed to generate PWs, the intensity of the PW can be set to the sufficient level so as to support the particular emission of the subject due to exposure to the PW. Similarly, GI output can be controlled to allow user selected dimming.

In addition to the LCD array 410 used in combination with the screen 408, the driver 412 may operate as a dimming mechanism to brighten or dim the lighting array 402, allowing further control of the intensity of both the GI light and the PW light. Some or all of the components of the lighting devices 200, 300, 400, such as dimming mechanisms, shutters, LCD arrays, and pixelated screens, can be combined into a lighting device for generating light for general illumination of a space and generating light of a particular wavelength at a sufficient intensity and duration reasonably expected to produce a particular emission from a subject different from an emission produced by exposure of the subject to GI light. The lighting devices disclosed herein integrate both a GI light source and a PW light source into a single lighting device, and are constructed such that the intended benefit of the PW light can be supported through control of the intensity, duration, and/or characteristics of the PW light.

Other lighting device arrangements permitting selective excitation of different types of fluorescent materials may be used to generate both GI lighting and PW lighting from one integrated lighting device. A few examples of such other arrangements may be found in U.S. Pat. No. 8,330,373, the full patent disclosure of which is incorporated entirely herein by reference.

The lighting devices of the machine vision systems disclosed may also be configured to produce a flashing pattern of a subject with the PW light as an additional method for producing particular emissions from a subject in a space. Referring back to FIGS. 1-4, the microcontroller 22, the microcontroller 129, the controllers 214 and 314, PW drivers 212 and 312, and/or GI drivers 208 and 310 may be configured to produce the above described flashing patterns. Microcontroller 22 can be programmed to power drivers 21a and/or 21b to alternate between power ON and OFF states so as to produce a flashing pattern. Similarly, microcontroller 129 can be programmed to power the drivers 121, 123, 125, and/or 127 to alternate between power ON and OFF states so as to produce a flashing pattern. Additionally, since the lighting device 200 is capable of producing particular wavelengths of PW light at sufficient intensities and for sufficient durations to produce the aforementioned particular emissions utilizing dimming mechanisms, the PW drivers 212 can configured cycle through periodic intensity changes to regulate a frequency at which the PW light is dimmed, thereby producing flashing patterns of PW light that is output. Similarly, the shutters 316a and 316b of lighting device 300 can be configured to open and close at particular frequencies to produce flashing patterns of PW light. As an example, lighting systems 200 and 300 can be configured to produce flashing patterns to cause subjects in the room to appear to flash.

Flashing patterns can also be produced with the lighting systems described with respect to FIG. 5. Different combinations of wavelengths produced by the fluorescent phosphor materials in the screen 408 can be used to produce the same color point, such as the color point desired for general illumination of the space. The screen 408 can be manufactured such that the screen 408 includes a pixel for each wavelength in the spectrum. As such, the LCDs 410 may be controlled via the controller 414 to either slowly or rapidly change the combination of wavelengths used for general illumination while keeping the color point of the general illumination light the same. By changing, back and forth over a period of time, the combination of wavelengths (e.g., the spectra) while keeping the color point of the general illumination the same, passive subjects in the space with optical characteristics responsive to the changing spectra will flash while the space remains under general illumination. Thus, the PW generated is the wavelength at which the passive subject in the room flashes under such changes. The slow or rapid change causes the PW to change in intensity, and the subject(s) responsive to the changing intensity of the PW appear to flash as the intensity changes.

This flashing pattern may be done with any wavelength of light that can be produced by the fluorescent phosphor materials. For example, signs may be placed in the space that flash when exposed to ultraviolet light, or other subjects such as ink pens will flash in response to changing intensities of particular wavelengths of visible light based on the subjects optical properties. The machines disclosed for use in machine vision applications can be configured to detect the flashing subjects for detecting a characteristic of the subject for an operation of the machine. For example, a machine can be configured to display the subject flashing to a user of a display. In another example, a machine uses a filter that is calibrated to the flashing frequency of the PW light output and/or the flashing frequency of the particular emissions from the subject to detect the subject.

Referring generally to FIGS. 6A-8C, further examples of systems for machine vision utilizing the disclosed machines and lighting systems are illustrated. The illustrated systems include lighting devices, spaces, machines, image capture devices, machine vision processing systems, particular emissions from subjects, and emissions from subjects produced by exposure to GI light. Each of the devices, machines, spaces, and emissions are similar to those described earlier, and the illustrated systems of FIGS. 6A-8C can incorporate any number of variations and combinations of the systems disclosed above.

Figure 6A:
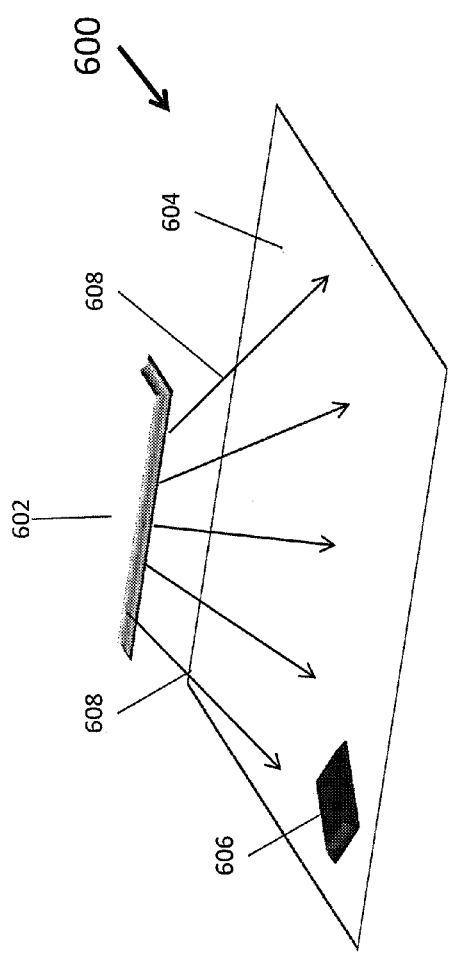
FIGS. 6A-6B are illustrations showing a system where particular emissions are produced.
Figure 6B:
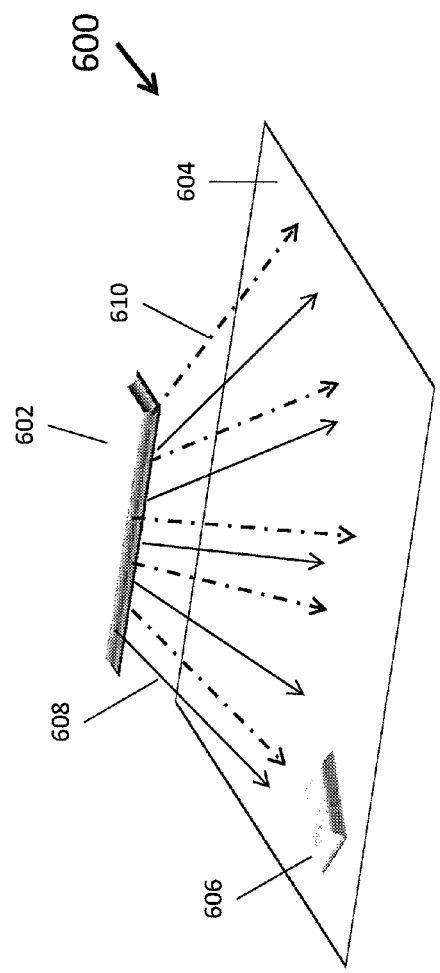

FIGS. 6A and 6B illustrate an example of a system for producing a particular emission in the visible spectrum from a subject different from an emission produced by exposure of the subject to GI light. At FIG. 6A, the system 600 includes a lighting device 602, a space 604 and a subject in the space 606. The lighting device is outputting only GI light 608. For illustrative purposes, it is shown that the subject 606 appears visibly darker (e.g., does not emit much visible light) due to exposure to the GI light 608. At FIG. 6B, the lighting device 602 is outputting both GI light 608 and PW light 610. The PW light 610 is of a sufficient intensity and/or other parameter to produce a particular emission from the subject 606 different from the emission produced by exposure of the subject 606 to the GI light 608 as was illustrated in FIG. 6A. For illustration purposes, the subject 606 is shown to produce a gray particular emission due to exposure of the PW light 610. In the example of system 600, the particular emission of the subject 606 is visible and can be detected without the use of a tuned capturing device.

FIGS. 7A-7C illustrate an example of a machine vision system for producing a particular emission from a subject different from an emission produced by exposure of the subject to GI light that is outside the visible spectra and is detectable by an image capture device of a machine for use in machine vision. At FIG. 7A, the system 700 includes a lighting device 702, a space 704 and a subject in the space 706. The lighting device is outputting only GI light 708. For illustrative purposes, it is shown that the subject 706 appears visibly darker (e.g. does not emit much visible light) due to exposure to the GI light 708. At FIG. 7B, the lighting device 702 is outputting both GI light 708 and PW light 710. The PW light 710 is of a sufficient intensity and/or other parameter to produce a particular emission from the subject 706 different from the emission produced by exposure of the subject 706 to the GI light 708. However, in the example illustrated at FIG. 7B, the PW light 710 produces a particular emission of the subject 706 that is not in the visible spectra. As shown, the visual appearance of the subject 706 is not altered by the output of the PW light 710. At FIG. 7C, an image capture device 712 in a machine for machine vision is shown viewing the space 704. The image capture device 712 can be configured to detect the particular emission of the subject 706, such that a machine vision processing system or other machine vision device integrating the image capture device 712 can detect a characteristic of the subject 706. Although the subject 706 is illustrated as gray in color, the image capture device 712 may be configured to represent the subject 706 or the particular emission of the subject 706 as any number of colors or other representations. In further examples, the visual appearance of subject 706 may be altered by exposure to the particular wavelength 710, but the altered visual appearance may not be the particular emission produced corresponding to the characteristic of the subject 706. For example, exposure to the PW light 710 cause the subject 706 to both visually emit a color different than emitted by exposure to GI light 708, and emit light of a wavelength outside the visible spectrum. The emission outside the visible spectrum can be the particular emission reasonably expected to be produced by the PW light 710, and the image capture device 712 can be configured to only detect the particular emission.

Figure 8A:
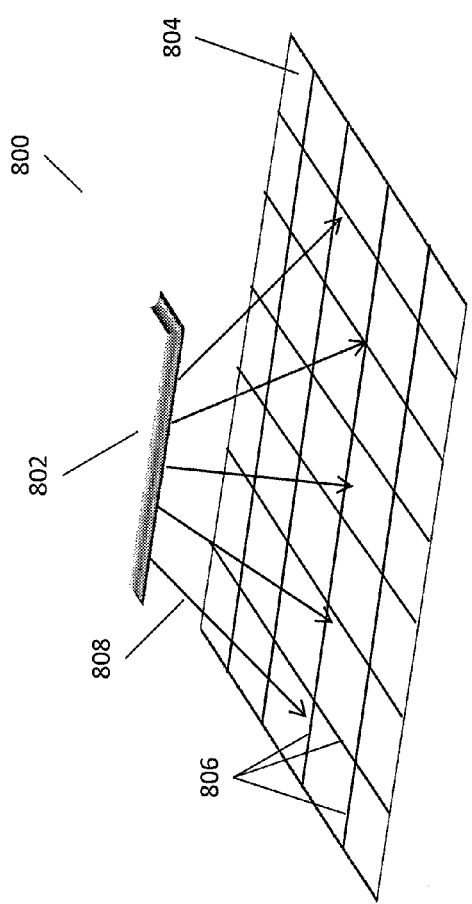
FIGS. 8A-8C are illustrations of systems showing particular emissions being produced in a space with a grid movement pattern for use in machine vision guided movement.
Figure 8B:
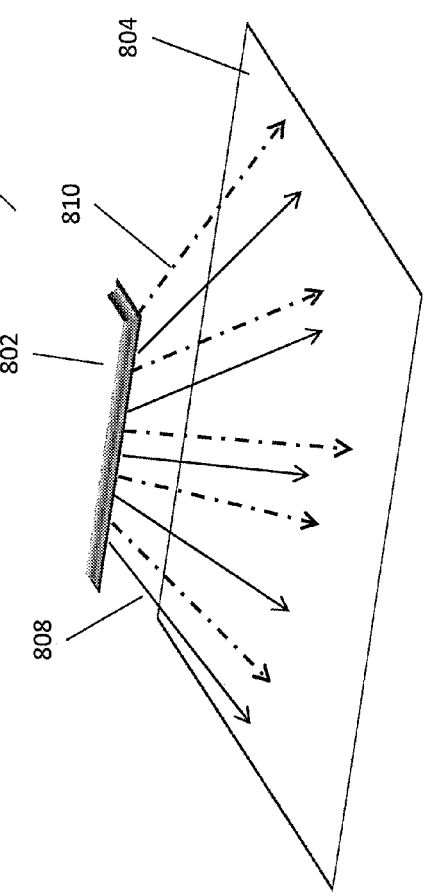
Figure 8C:
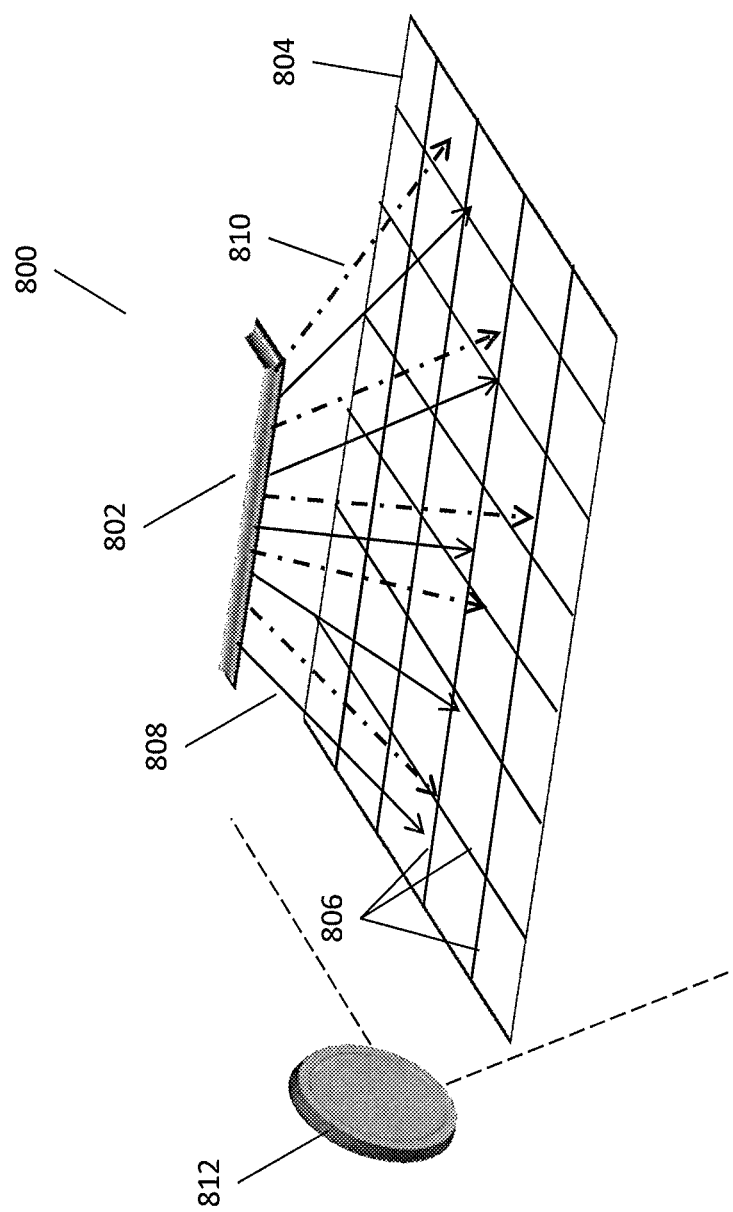

Another example of a machine vision system is illustrated at FIGS. 8A-8C. The system 800 includes a lighting device 802, a space 804, and a grid pattern 806 as a subject in the space 804. The grid pattern 806 can be a movement guidance pattern for a machine to detect the location of the grid 806 and operate the movement of the machine through the space 804 based on the detected location of the grid pattern 806. In FIG. 8A, the lighting device 802 is outputting GI light 808 only. The grid 806 is visible under exposure to GI light 808. In FIG. 8B, the lighting device 802 is outputting both GI light 808 and PW light 810. The grid 806 may be composed of a material (e.g., paint) of which the optical properties are known, such that, upon exposure to either PW light 810 or both GI light 808 and PW light 810, a particular emission from the grid 806 is produced such that the grid 806 appears of a visibly similar color as the rest of the space 804 (e.g., a created metamer for human vision). At FIG. 8C, an image capture device 812 of a machine is configured to detect and/or filter the particular emission of the grid 806 produced by exposure to the PW light (or combination of GI light 808 and PW light 810) at FIG. 8B. The image capture device 812 may be configured to both detect the particular emission of the grid 806 and filter the particular emission of the grid. 806 such that the characteristic of the grid 806 (e.g., the grid itself or the pattern of the grid), is visible in the captured image. The captured image may be received by a machine vision processing system (not shown), which may also or alternatively detect the particular emission and/or filter the particular emission such that the characteristic of the grid 806 can be processed for movement of the machine through the space 804.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A system, comprising:
   (I) a machine comprising:
      (a) an image capture device; and
      (b) a machine vision processing system, the machine vision processing system being configured to detect a characteristic of a subject in a space responsive to input from the image capture device for an operation of the machine at least in part based on detection of the characteristic of the subject; and
   (II) a lighting device, comprising:
      (i) a first light source configured to generate light for illumination of the space; and
      (ii) a second light source configured to generate, independent from the light for illumination, light of a particular wavelength to support the detection of the characteristic of the subject located in the space via the machine vision processing system wherein:
         the light of the particular wavelength is output from the lighting device at a sufficient intensity reasonably expected to produce a particular emission from the subject detectable via the image capture device different from an emission produced by exposure of the subject to the light for illumination output from the lighting device,
         the first and second light sources are integrated into the lighting device, and
         the characteristic of the subject is detectable based on imaging processing, by the machine vision processing system, of an image captured by the image capture device of the particular emission from the subject.

2. The system of claim 1, further comprising a controller providing control of the second light source independent from control of the first light source.

3. The system of claim 1, further comprising:
   at least one shutter coupled to a light output of the second source; and
   a controller coupled to the at least one shutter, the controller being configured to selectively permit light generated from the second light source to be output through the at least one shutter.

4. The system of claim 3, wherein the at least one shutter is a liquid crystal shutter, a mechanical shutter, or a microelectromechanical shutter.

5. The system of claim 1, wherein the machine vision processing system is configured to filter the particular emission from the subject such that the operation of the machine is at least in part based on the emission produced by exposure of the subject to the light for illumination.

6. The system of claim 1, wherein:
   the light for illumination of the space is in the visible spectrum, and
   the particular wavelength is such that the particular emission from the subject is outside the visible spectrum.

7. The system of claim 1, wherein the particular wavelength output from the lighting device is a wavelength reasonably expected to produce the particular emission from of at least one of a group consisting of: blood, dust, paint, and contaminant, as the subject.

8. The system of claim 1, wherein the particular wavelength is output at a sufficient intensity, for a sufficient duration, and at a predefined frequency to cause a flashing pattern of the particular emission from the subject.

9. The system of claim 1, wherein the machine vision processing system is configured to detect the characteristic of the subject at least in part based on a contrast difference between the particular emission from the subject and the emission produced by exposure of the subject to the light for illumination.

10. A system, comprising:
    (I) a machine comprising:
       (a) an image capture device; and
       (b) a machine vision processing system, the machine vision processing system being configured to detect a characteristic of a subject in a space responsive to input from the image capture device for an operation of the machine at least in part based on detection of the characteristic of the subject; and
    (II) a lighting device, comprising:
       (i) a first light source configured to generate light for illumination of the space; and
       (ii) a second light source configured to generate, independent from the light for illumination, light of a particular wavelength to support the detection of the characteristic of the subject via the machine vision processing system wherein:
          the light of the particular wavelength is output from the lighting device at a sufficient intensity reasonably expected to produce a particular emission from the subject detectable via the image capture device different from an emission produced by exposure of the subject to the light for illumination output from the lighting device,
          the first and second light sources are integrated into the lighting device, and
          the operation of the machine comprises movement of the machine throughout the space.

11. The system of claim 10, wherein:
    the machine vision processing system is further configured to detect a location of a movement grid pattern as the characteristic of the subject, and
    the operation of the machine comprises movement of the machine through the space at least in part based on the detected location of the movement grid pattern.

12. A method, comprising:
    generating, from a first light source integrated into a lighting device, light for illumination of a space;
    generating, from a second light source integrated into the lighting device and independently from the generating of light for illumination of the space, light of a particular wavelength to support detection of a characteristic of a subject via a machine vision processing system of a machine, the subject being located in the space;
    outputting the light for illumination of the space;
    outputting the light of the particular wavelength at a sufficient intensity reasonably expected to produce a particular emission from a subject in the space detectable via an image capture device in the machine, the particular emission being different from an emission produced by exposure of the subject to the light for illumination;
    receiving, via the machine vision processing system of the machine, input from the image capture device, the input comprising the particular emission from the subject detected by the image capture device;
    detecting, via the machine vision processing system, the characteristic of the subject in the space from the input received from the image capture device; and
    controlling operation of the machine at least in part based on the detected characteristic of the subject.

13. The method of claim 12, further comprising:
filtering, with the machine vision processing system, the particular emission from the subject; and
wherein the controlling step comprises controlling operation of the machine at least in part based on the emission produced by exposure of the subject to the light for illumination.

14. The method of claim 12, wherein the step of detecting of the characteristic of the subject in the space comprises:
image processing the input received from the image capture device to detect the characteristic of the subject.

15. A method, comprising
generating, from a first light source integrated into a lighting device, light for illumination of a space;
generating, from a second light source integrated into the lighting device and independently from the generating of light for illumination of the space, light of a particular wavelength to support detection of a characteristic of a subject via a machine vision processing system of a machine;
outputting the light for illumination of the space;
outputting the light of the particular wavelength at a sufficient intensity reasonably expected to produce a particular emission from a subject in the space, detectable via an image capture device in the machine, different from an emission produced by exposure of the subject to the light for illumination;
receiving, via the machine vision processing system of the machine, input from the image capture device, the input comprising the particular emission from the subject detected by the image capture device;
detecting, via the machine vision processing system, the characteristic of the subject in the space from the received input; and
controlling operation of the machine at least in part based on the detected characteristic of the subject,
wherein the step of controlling operation of the machine comprises guiding movement of the machine through the space at least in part based on the detected characteristic of the subject in the space.

16. A lighting device, comprising:
(i) a first light source configured to generate light for illumination of a space;
(ii) a second light source configured to generate, independent from the light for illumination, light of a particular wavelength to support detection of a characteristic of a subject for responsive control of a machine; and
(iii) a controller configured to alter the generation of the particular wavelength by the second light source to coordinate operations of the second light source to operations of a machine that responds to the particular wavelength of light, wherein:
the light of the particular wavelength is output from the lighting device at a sufficient intensity reasonably expected to produce a particular emission from the subject different from an emission produced by exposure of the subject to the light for illumination, and
the first and second light sources are integrated into the lighting device.

17. The device of claim 16, wherein the light of the particular wavelength is outputted at a sufficient intensity, for a sufficient duration, and of a particular parameter to produce the particular emission from the subject in a flashing pattern.

18. The device of claim 16, wherein the light for illumination generated by the first light source and the light of the particular wavelength generated by the second light source are generated simultaneously.

19. The device of claim 16, wherein the controller is further configured to control the second light source independent from control of the first light source.

20. The device of claim 16, wherein the machine and the lighting device are located remote from one another.

* * * * *